United States Patent
Kovar et al.

(10) Patent No.: US 7,597,878 B2
(45) Date of Patent: *Oct. 6, 2009

(54) OPTICAL FLUORESCENT IMAGING

(75) Inventors: Joy Kovar, Lincoln, NE (US); Jiyan Chen, Lincoln, NE (US); Daniel R. Draney, Lincoln, NE (US); D. Michael Olive, Lincoln, NE (US); William M. Volcheck, Lincoln, NE (US); Xinshe Xu, Lincoln, NE (US); Ananda G. Lugade, Austin, TX (US); Narasimhachari Narayanan, Westford, MA (US)

(73) Assignee: Li-Cor, Inc., Lincoln, NE (US)

( * ) Notice: Subject to any disclaimer, the term of this patent is extended or adjusted under 35 U.S.C. 154(b) by 510 days.

This patent is subject to a terminal disclaimer.

(21) Appl. No.: 11/419,457

(22) Filed: May 19, 2006

(65) Prior Publication Data

US 2006/0280688 A1    Dec. 14, 2006

Related U.S. Application Data

(60) Continuation-in-part of application No. 11/267,643, filed on Nov. 4, 2005, now Pat. No. 7,504,089, which is a division of application No. 10/354,812, filed on Jan. 28, 2003, now Pat. No. 6,995,274, which is a continuation of application No. PCT/US01/29385, filed on Sep. 18, 2001.

(60) Provisional application No. 60/233,511, filed on Sep. 19, 2000.

(51) Int. Cl.
  *A61B 10/00* (2006.01)
  *A61B 5/00* (2006.01)
  *A61B 8/00* (2006.01)

(52) U.S. Cl. ............ 424/9.6; 424/1.11; 424/1.65; 424/9.1

(58) Field of Classification Search ........ 424/1.11, 424/1.37, 1.49, 1.65, 1.69, 1.73, 9.3, 9.4, 424/9.5, 9.6, 9.7; 548/427, 455; 530/300, 530/387.1; 536/1.11, 322; 514/773, 836

See application file for complete search history.

(56) References Cited

U.S. PATENT DOCUMENTS

| 5,268,486 A | 12/1993 | Waggoner et al. |
|---|---|---|
| 5,519,145 A | 5/1996 | Fabricius et al. |
| 5,569,587 A | 10/1996 | Waggoner |
| 5,571,388 A | 11/1996 | Patonay et al. |
| 5,877,310 A | 3/1999 | Reddington et al. |
| 6,027,709 A | 2/2000 | Little et al. |
| 6,083,485 A | 7/2000 | Licha et al. |
| 6,136,612 A | 10/2000 | Della Ciana et al. |
| 6,329,531 B1 | 12/2001 | Turner et al. |
| 6,448,008 B1 | 9/2002 | Caputo et al. |
| 6,534,041 B1 | 3/2003 | Licha et al. |
| 6,641,798 B2 | 11/2003 | Achilefu et al. |
| 6,642,375 B2 | 11/2003 | Inomata et al. |
| 6,649,335 B2 | 11/2003 | Missfeldt |
| 6,747,159 B2 | 6/2004 | Caputo et al. |
| 6,761,878 B2 | 7/2004 | Achilefu et al. |
| 6,989,140 B2 | 1/2006 | Tidmarsh et al. |
| 6,995,274 B2 * | 2/2006 | Lugade et al. ............ 548/427 |
| 2004/0014981 A1 | 1/2004 | Lugade et al. |
| 2005/0214221 A1 | 9/2005 | Poss et al. |

FOREIGN PATENT DOCUMENTS

| CA | 2145405 | 2/1995 |
|---|---|---|
| DE | 43 26 466 | 2/1995 |
| EP | 0 580 145 A2 | 1/1994 |
| EP | 0 580 145 A3 | 1/1994 |
| EP | 1065250 A1 | 1/2001 |
| EP | 1223197 A2 | 7/2002 |
| EP | 1223197 A3 | 7/2002 |
| JP | 6-145539 | 5/1994 |
| WO | WO 97/13810 A1 | 4/1997 |
| WO | WO 98/52609 A1 | 11/1998 |
| WO | WO 00/16810 A1 | 3/2000 |
| WO | WO 02/24815 A1 | 3/2002 |
| WO | WO 02/058370 A1 | 7/2002 |
| WO | WO 02/074171 A1 | 9/2002 |
| WO | WO 03/079015 A1 | 3/2003 |

(Continued)

OTHER PUBLICATIONS

Narayanan, N., et al., A New Method For the Synthesis of Heptamethine Cyanine Dyes: Synthesis of New Near Infrared Fluorescent Labels, Journal of Organic Chemistry, American Chemical Society, 1995, pp. 2391-2395, vol. 60, XP 002065376, ISSN: 0022-3263.

(Continued)

*Primary Examiner*—D L Jones
(74) *Attorney, Agent, or Firm*—Townsend and Townsend and Crew

(57) ABSTRACT

Compounds and methods are disclosed that are useful for noninvasive imaging in the near-infrared (NIR) spectral range. The NIR is highly sensitive for tumor detection and tracking. The application discloses targeting a tumor-enriched cell surface receptor with a ligand-conjugated fluorescent probe, which specifically allows detection of the tumor relative to the negligible animal autofluorescence.

38 Claims, 7 Drawing Sheets

FOREIGN PATENT DOCUMENTS

| WO | WO 2005/030265 A2 | 4/2005 |
| WO | WO 2005/058371 A1 | 6/2005 |
| WO | WO 2005/058372 A2 | 6/2005 |
| WO | WO 2007/005222 A2 | 1/2007 |
| WO | WO 2007/005222 A3 | 1/2007 |

OTHER PUBLICATIONS

International Search Report for PCT/US01/29385, dated Feb. 25, 2002.

Weissleder, Ralph, "A clearer vision in vivo imaging," Nature Biotechnology, URL: http://biotech.nature.com, vol. 11, pp. 316-317, (Apr. 2001).

International Search Report mailed on Oct. 5, 2007, for PCT Application No. PCT/US2007/068564 filed on May 9, 2007, five pages.

Becker, Andreas et al.; Receptor-Targeted Optical Imaging of Tumors with Near-Infrared Fluorescent Ligands; *Nature Technology;* 19:327-331 (Apr. 2001).

Bugaj, Joseph E., et al.; Novel Cluorescent Contrast Agents for Optical Imaging of In Vivo Tumors Based on a Receptor-Targeted Dye-Peptide Conjugate Platform; *Journal of Miomedical Optics;* 6(2):122-133 (Apr. 2001).

Licha, Kai et al.; Hydrophilic Cyanine Dyes as Contrast Agents for Near-Infrared Tumor Imaging: Synthesis, Photophysical Properties and Spectroscopic In Vivo Characterization; *Photochemistry and Photobiolo;* 72(3):392-398 (2000).

Lin, Yuhui et al.; Novel Near-Infrared Cyanine Fluorchromes: Synthesis, Properties and Bioconjugation; *Bioconjugate Chm.;* 13:605-610 (2002).

Weissleder, Ralph et al.; In Vivo Imaging of Tumors with Protease-Activated Near-Infrared Fluorescent Probes; *Nature Biotechnology;* (17):375-378 (Apr. 1999).

Zaheer, A., et al.; In Vivo Near Infrared Fluorescence Imaging of Osteoblastic Activity; *Nature Biotechnology;* 19(12):1148-1154 (2001).

* cited by examiner

OPTICAL FLUORESCENT IMAGING

CROSS-REFERENCES TO RELATED APPLICATIONS

The present application is a continuation-in-part of U.S. patent application Ser. No. 11/267,643, filed Nov. 4, 2005 now U.S. Pat. No. 7,504,089, which application is a divisional application of U.S. patent application Ser. No. 10/354,812, filed Jan. 28, 2003, now U.S. Pat. No. 6,995,274, which application is a continuation of PCT Application No. US01/29385 filed on Sep. 18, 2001, which application claims the benefit of U.S. Provisional Patent Application No. 60/233,511, filed on Sep. 19, 2000, all of which are hereby incorporated by reference.

BACKGROUND OF THE INVENTION

Cyanine dyes have been widely used for labeling ligands or biomolecules for a variety of applications such as DNA sequencing. See, for example, U.S. Pat. No. 5,571,388, incorporated herein by reference, for exemplary methods of identifying strands of DNA using cyanine dyes. Scientists favor using cyanine dyes in biological applications because, among other reasons, many of these dyes operate in the near IR (NIR) region of the spectrum (600-1000 nm). This makes these cyanine dyes less susceptible to interference from auto fluorescence of biomolecules.

Other advantages of cyanine dyes include: 1) cyanine dyes strongly absorb and fluoresce light; 2) many cyanine dyes do not rapidly bleach under the fluorescence microscope; 3) cyanine dye derivatives can be made that are simple and effective coupling reagents; 4) many structures and synthetic procedures are available and the class of dyes is versatile; and 5) cyanine dyes are relatively small (a typical molecular weight is about 1,000 daltons) so they do not cause appreciable steric interference in a way that might reduce the ability of a labeled biomolecule to reach its binding sight or carry out its function.

Despite their advantages, many of the known cyanine dyes have a number of disadvantages. Some known cyanine dyes are not stable in the presence of certain reagents that are commonly found in bioassays. Such reagents include ammonium hydroxide, dithiothreitol (DTT), primary and secondary amines, and ammonium persulfate (APS). Further, some known cyanine dyes lack the thermal and photostability that is necessary for biological applications such as DNA sequencing and genotyping.

For these reasons, improved, stable cyanine dyes are needed, especially for use in labeling biomolecules, and in vivo imaging for cancer diagnosis, prognosis as well as other diseases.

Human prostate cancer initially arises as a neoplasia within the prostate epithelium. Progression of the tumor to invasive, metastatic disease may occur over a period of years, and is delayed by androgen ablation therapies in early stages. Tumor cells that resume growth independently of androgens will frequently metastasize to lymph nodes and bone. Complications from bone metastasis are the most common cause of prostate cancer mortality.

EGF receptor expression is elevated approximately 100-fold over normal cellular levels in many tumor cell types, including prostate, making it a good general biomarker for tumor targeting. Its ligand, EGF, has been labeled successfully with FITC to characterize receptor binding and endocytosis (see, Carraway, K. L. 3rd and R. A. Cerione. 1993. *Biochemistry* 32(45):12039-12045), and with Cy5.5 to monitor molecular targeting therapy in breast cancer xenografts in vivo (see, Shi K., et al. 2003. *Cancer Research* 63:7870-7875). However, neither FITC nor Cy5.5 afford the requisite sensitivity for optical imaging.

There exists a need for sensitive compositions and methods to detect and measure an internal target non-invasively. Such compositions and methods would facilitate the analysis of responses to various therapies. The present invention satisfies these and other needs.

BRIEF SUMMARY OF THE INVENTION

The methods, compounds, dyes, and dye-labeled biomolecules of the present invention solve at least some of the problems of the above-described art.

In one aspect of the invention, a compound of the formula (I) is provided:

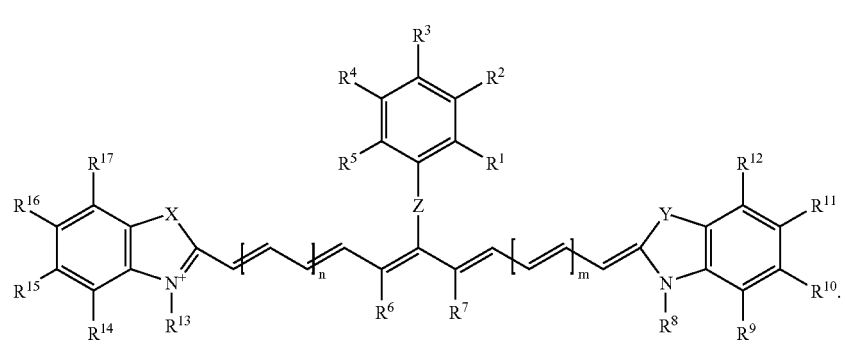

(I)

Z is O, S, or $NR^{35}$ wherein $R^{35}$ is H or alkyl; $R^1$-$R^5$ are each independently H, alkyl, halo, carboxyl, amino, or $SO_3^-Cat^+$, wherein $Cat^+$ is a cation and at least one of $R^1$-$R^5$ is $SO_3^-Cat^+$; $R^6$ and $R^7$ are each H, alkyl, or optionally, together with the

group to which they are bonded, form a ring; m and n are each independently integers from 0 to 5; X and Y are each independently O, S, Se, or $CR^{19}R^{20}$, wherein $R^{19}$ and $R^{20}$ are each independently alkyl, or optionally form a ring together with the carbon atom to which they are bonded; $R^8$ and $R^{13}$ are each independently alkyl, $(CH_2)_rR^{25}$ or $(CH_2)_rR^{18}$; wherein at least one of $R^8$ and $R^{13}$ is $(CH_2)_rR^{18}$ and wherein r is an integer from 1 to 50, and $R^{25}$ is a non-reactive functional group, for example, that does not directly react with a carboxyl, hydroxyl, amino, or a thiol group, and $R^{18}$ is a functional group that can react with a carboxyl, hydroxyl, amino, or thiol group; and $R^9$-$R^{12}$ and $R^{14}$-$R^{17}$ are each independently H, alkyl, halo, amino, sulfonato, $R^{21}COOH$, $R^{21}OR^{22}$, $R^{21}SR^{22}$, or $R^{21}COOR^{22}$ wherein $R^{21}$ is a bond or alkylene and $R^{22}$ alkyl, or optionally $R^{11}$ and $R^{12}$ together with the atoms to which they are bonded form an aromatic ring, or optionally $R^{16}$ and $R^{17}$ together with the atoms to which they are bonded form an aromatic ring.

In another aspect of the invention, a compound of the formula (V) is provided:

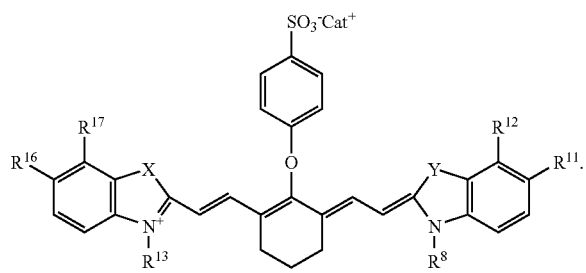

(V)

Cat$^+$ is a cation; X and Y are each independently O, S, Se, or $(CH_3)_2C$; and $R^8$ and $R^{13}$ are each independently alkyl, $(CH_2)_rR^{25}$ or $(CH_2)_rR^{18}$; wherein at least one of $R^8$ and $R^{13}$ is $(CH_2)_rR^{18}$ and wherein r is an integer from 1 to 20, and $R^{25}$ is a non-reactive functional group that does not directly react with a carboxyl, hydroxyl, amino, or a thiol group, and $R^{18}$ is a functional group that can react with a carboxyl, hydroxyl, amino, or thiol group; $R^{11}$ and $R^{12}$ are either H, sulfonato, or together with the atoms to which they are bonded form an aromatic ring; and $R^{16}$ and $R^{17}$ are either H, sulfonato, or together with the atoms to which they are bonded form an aromatic ring. In order to achieve charge neutrality, a skilled person will understand that after the first additional "sufonato" group from $R^{11}$, $R^{12}$, $R^{16}$ and $R^{17}$ a Cat$^+$ is added. The first "sufonato" group is neutralized from the quaternary nitrogen.

In another aspect of the invention, a method of labeling a biomolecule using a dye of the formula (I) comprises reacting a dye of the formula (I) with the biomolecule. The resulting dye-labeled biomolecule is still another aspect of the invention.

In another aspect of the invention, a method of labeling a biomolecule using a dye of the formula (V) comprises reacting a dye of the formula (V) with the biomolecule. The resulting dye-labeled biomolecule is still another aspect of the invention.

In yet another aspect of the invention, a kit for labeling biomolecules comprises a dye of the formula (I) and a buffer. Similarly, in another aspect of the invention, a kit for labeling biomolecules comprises a dye of the formula (v) and a buffer.

In yet another aspect, the present invention provides a compound of the formula XXI:

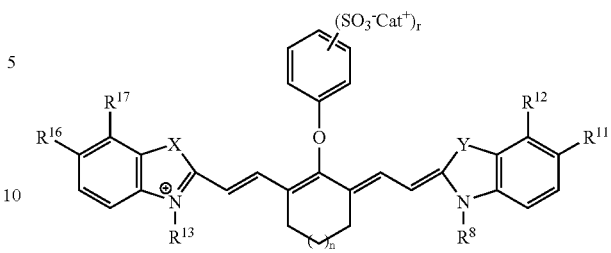

wherein Cat$^+$ is a cation; r is an integer equal to 1, 2 or 3; X and Y are each independently O, S, Se, or $(CH_3)_2C$; and $R^8$ and $R^{13}$ are each independently alkyl, L—$R^{25}$ or L—B; wherein at least one of $R^8$ and $R^{13}$ is L—B; $R^{25}$ is a non-reactive functional group that does not directly react with a carboxyl, hydroxyl, amino, or a thiol group; L is a linker; B is a ligand; n is 0, 1, 2 or 3; $R^{11}$ and $R^{12}$ are each independently F, H, sulfonato, or together with the atoms to which they are bonded form an aromatic ring; and $R^{16}$ and $R^{17}$ are each independently F, H, sulfonato, or together with the atoms to which they are bonded form an aromatic ring. In order to achieve charge neutrality, a skilled person will understand that after the first additional "sufonato" group from $R^{11}$, $R^{12}$, $R^{16}$ and $R^{17}$ a Cat$^+$ is added. The first "sulfonato" group is neutralized from the quaternary nitrogen. Preferably, r is 1.

The present invention provides the foregoing and other features, and the advantages of the invention will become further apparent from the following detailed description of the presently preferred embodiments, read in conjunction with the accompanying examples. The detailed description and examples are merely illustrative of the invention and do not limit the scope of the invention, which is defined by the appended claims and equivalents thereof.

DETAILED DESCRIPTION OF THE INVENTION

I. Definitions

Figure 1:
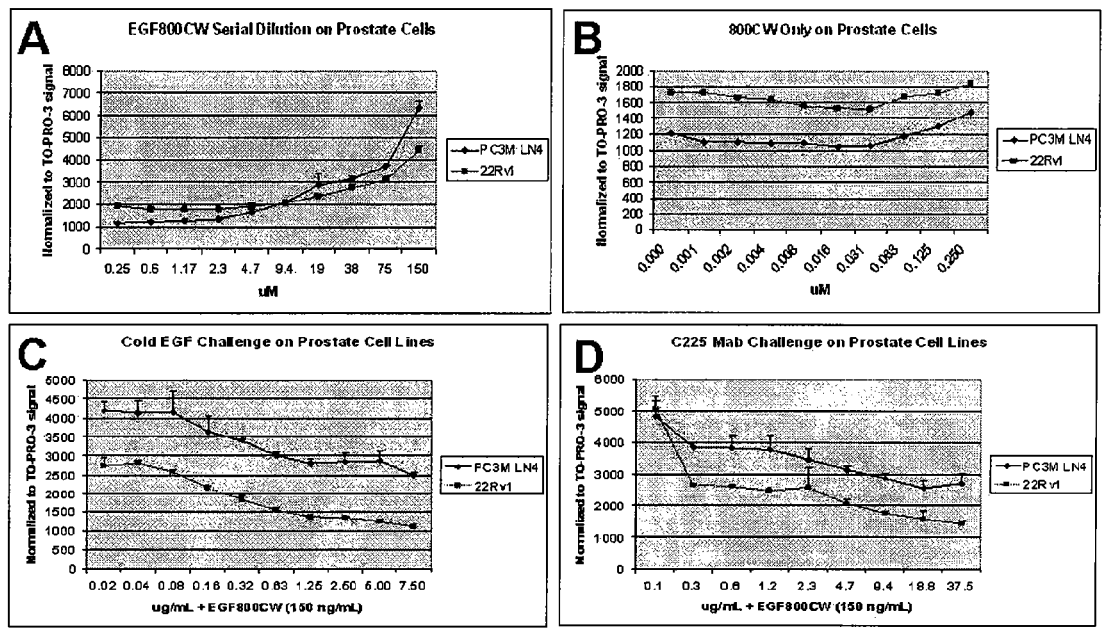
FIG. 1 (Panel A-D) illustrates in vitro in-cell western analysis characterizing the effectiveness of EGF-Dye 8b (of Example 8) in PC3M LN4 and 22Rv1 cell lines. In panel A, binding of the EGF-Dye 8b probe to PC3M-LN4 and 22Rv1 cells is plotted. Panel B illustrates the low affinity of unconjugated Dye 8b and corresponds to the baseline level seen in Panel A. In panels C and D, binding of the labeled Dye 8b was effectively blocked by pre-treatment of cells with unlabeled EGF (C) or C225 (D).

"Alkanoyl" means an alkyl-C(O) group wherein the alkyl group is as defined herein. Representative alkanoyl groups include methoyl, ethoyl, and the like.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" means an alkyl-O-alkylene-group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" means an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkylcarbamoyl" means an alkyl-NH—CO— group wherein alkyl group is defined herein. Preferred alkylcarbamoyl groups are those wherein the alkyl group is lower alkyl.

"Alkoxycarbonylalkyl" means an alkyl-O—CO-alkylene-group wherein alkyl and alkylene are as defined herein. Representative alkoxycarbonylalkyl include methoxycarbonylmethyl, and ethoxycarbonylmethyl, methoxycarbonyl ethyl, and the like.

"Alkyl" means an aliphatic hydrocarbon group, which may be straight or branched-chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means 1 to about 6 carbon atoms, preferably about 5 carbon atoms in the chain, which may be straight or branched. The alkyl is optionally substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, 1-butyl, n-pentyl, 3-pentyl, methoxyethyl, carboxymethyl, methoxycarbonylethyl, benzyloxycarbonylmethyl, and pyridylmethyloxycarbonylmethyl.

In certain other aspects, "alkyl" is a saturated aliphatic group, including substituted and unsubstituted straight-chain alkyl groups, substituted and unsubstituted branched alkyl groups, and substituted and unsubstituted cycloalkyl groups. The term "alkyl" includes alkoxy, haloalkyl, hydroxyalkyl, and alkyloxyalkyl ether species. In preferred embodiments, a straight chain or branched chain alkyl has 50 or fewer carbon atoms in its backbone, more preferably 30 or fewer, and most preferably 10 or fewer. Preferred cycloalkyls have from 3-10 carbon atoms in their ring structure, and more preferably have 3-6 carbon atoms. "Lower alkyl" means an alkyl group having from 1-10 carbon atoms in its backbone, more preferably from 1-6 carbon atoms. Alkyl cyclic groups can be single or polycyclic, containing between 3 to 12 atoms per ring, but preferably between 1 and 9 atoms in the backbone. Preferred substituents on an alkyl backbone include substituted or unsubstituted alkyl radicals, halo, carboxyl, amino, and sulfanato groups.

In certain other aspects, "alkenyl" and "alkynyl" are unsaturated aliphatic substituents analogous in length and possible substitution to the alkyl radicals described above, but which contain at least one double or triple bond, respectively.

"Alkylene" means a straight or branched bivalent hydrocarbon chain of 1 to about 6 carbon atoms. The alkylene is optionally substituted with one or more "alkylene group substituents" which may be the same or different, and include halo, cycloalkyl, hydroxy, alkoxy, carbamoyl, carboxy, cyano, aryl, heteroaryl or oxo. The alkylene is optionally interrupted by a heteroatom, i.e., a carbon thereof is substituted by, —O—, —S($=$O)$_m$ (where m is 0-2), or –NR'- (where R' is lower alkyl). Preferred alkylene groups are the lower alkylene groups having 1 to about 4 carbon atoms. Representative alkylene groups include methylene, ethylene, and the like.

"Alkyleneoxycarbonyl, means an ester group; i.e., an alkylene-O—CO— group wherein alkylene is as defined herein.

"Alkylenecarbamoyl means an alkylene-NH—CO— group wherein alkylene group is defined herein. Preferred alkylenecarbamoyl groups are those wherein the alkylene group is lower alkylene.

"Alkylenesulfonyl" means an alkylene-SO$_2$— group wherein the alkylene group is as defined herein. Preferred alkylenesulfonyl groups are those wherein the alkylene group is lower alkylene.

"Alkylenesulfonylcarbamoyl means an alkylene-SO$_2$—NH—CO— group wherein alkylene group is defined herein.

"Alkenylene" means a straight or branched bivalent hydrocarbon chain containing at least one carbon-carbon double bond. The alkenylene is optionally substituted with one or more "alkylene group substituents" as defined herein. The alkenylene is optionally interrupted by a heteroatom, i.e., a carbon thereof is substituted by, —O—, —S(O)$_m$ (where m is 0-2), or —NR'— (where R' is lower alkyl). Representative alkenylene include —CH$=$CH—, —CH$_2$CH$=$CH—, —C(CH$_3$)$=$CH—, —CH$_2$ CH$=$CHCH$_2$—, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$— group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon-carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O— group wherein the alkynyl group is as defined herein. Representative alkynyloxy groups include propynyloxy, 3-butynyloxy, and the like.

"Amino" means a group of formula Y$_1$Y$_2$N— wherein Y$_1$ and Y$_2$ are independently hydrogen; acyl; or alkyl, or Y$_1$ and $Y_2$ taken together with the N through which $Y_1$ and $Y_2$ are linked form a 4 to 7 membered azaheterocyclyl. Representative amino groups include amino ($H_2N$—), methylamino, dimethylamino, diethylamino, and the like. Alternatively, "amino" is an —NRR' group where R and R' can be the same or different, and either can be H or alkyl. Preferably, at least one of R and R' is H. Optionally, an additional substituent can be added, making a quaternary ammonium ion.

"Aminoalkyl" means an amino-alkylene-group wherein amino and alkylene are defined herein. Representative aminoalkyl groups include aminomethyl, aminoethyl, dimethylaminomethyl, and the like.

"Aralkenyl" means an aryl-alkenylene-group wherein aryl and alkenylene are as defined herein. Preferred aralkenyls contain a lower alkenylene moiety. A representative aralkenyl group is 2-phenethenyl.

"Aralkyloxy" means an aralkyl-O— group wherein aralkyl is defined herein. Representative aralkyloxy groups include benzyloxy, naphth-1-ylmethoxy, naphth-2-ylmethoxy, and the like.

"Aralkyloxyalkyl" means an aralkyl-O-alkylene-group wherein aralkyl and alkylene are as defined herein. A representative aralkyloxyalkyl group is benzyloxyethyl.

"Aralkyloxycarbonyl" means an aralkyl-O—CO-group wherein aralkyl is as defined herein. A representative aralkoxycarbonyl group is benzyloxycarbonyl.

"Aralkyl" means an aryl-alkylene-group wherein aryl and alkylene are as defined herein. Preferred aralkyls contain a lower alkyl moiety. Representative aralkyl groups include benzyl, 2-phenethyl, naphthlenemethyl, and the like.

"Aralkylthio" means an aralkyl-S-group wherein aralkyl is as defined herein. A representative aralkylthio group is benzylthio.

"Aroyl" means an aryl-CO— group wherein aryl is defined herein. Representative aroyl include benzoyl, naphth-1-oyl and naphth-2-oyl.

"Aryl" means an aromatic monocyclic or multicyclic ring system of 6 to about 14 carbon atoms, preferably of 6 to about 10 carbon atoms. The aryl is optionally substituted with one or more "ring system substituents" which may be the same or different, and are as defined herein. Representative aryl groups include phenyl and naphthyl.

"Arylene" means a bivalent aromatic monocyclic or multicyclic ring system radical of 6 to about 14 carbon atoms, preferably of 6 to about 10 carbon atoms. The arylene radical is optionally substituted with one or more "ring system substituents" which may be the same or different, and are as defined herein. Representative aryl groups include phenylene and naphthylene.

"Arylenensulfonyl" means an arylene-$SO_2$— group wherein the arylene group is as defined herein.

"Aryleneoxycarbonyl" means an ester group; i.e., an arylene-O—CO— group wherein arylene is as defined herein.

"Arylenecarbamoyl" means an arylene-NHCO— group, wherein arylene is defined herein.

"Arylenesulfonylcarbamoyl" means an arylene-$SO_2$—NH—CO— group wherein arylene is defined herein.

"Arylsulfinyl" means an aryl-SO— group wherein the aryl group is as defined herein.

"Aralkynyl" means an aryl-alkynylene- group wherein aryl and alkynylene are defined herein. Representative aralkynyl groups include phenylacetylenyl and 3-phenylbut-2-ynyl.

"Arylcarbamoyl" means an aryl-NHCO— group, wherein aryl is defined herein.

"Arylsulfinyl" means an aryl-SO— group wherein the aryl group is as defined herein. Preferred arylsulfinyl groups are those wherein the aryl group is a substituted phenyl.

"Arysulfonyl" means an aryl-$SO_2$— group wherein the aryl group is as defined herein. Preferred arylsulfonyl groups are those wherein the aryl group is a substituted phenyl.

"Arylsulfonylcarbamoyl" means an aryl-$SO_2$—NH—CO— group wherein aryl group is defined herein. Preferred arylsulfonylcarbamoyl groups are those wherein the aryl group is a substituted phenyl.

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aryl groups include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, etc. The aryl group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Biomolecule" is a natural or synthetic molecule for use in biological systems. Preferred biomolecules include a protein, a peptide, an enzyme substrate, a hormone, an antibody, an antigen, a hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

"Benzyl" means a phenyl-$CH_2$— group. Substituted benzyl means a benzyl group in which the phenyl ring is substituted with one or more ring system substituents. Representative benzyl include 4-bromobenzyl, 4-methoxybenzyl, 2,4-dimethoxybenzyl, and the like.

"Carbamoyl" means a group of formula $Y_1Y_2$ NCO— wherein $Y_1$ and $Y_2$ are independently hydrogen; acyl; or alkyl, or $Y_1$ and $Y_2$ taken together with the N through which $Y_1$ and $Y_2$ are linked form a 4 to 7 membered azaheterocyclyl. Representative carbamoyl groups include carbamyl ($H_2$ NCO—), dimethylaminocarbamoyl ($Me_2$ NCO—), and the like.

"Carboxy" and "carboxyl" mean a HO(O)C— group (i.e. a carboxylic acid).

"Carboxyalkyl" means a HO(O)C-alkylene-group wherein alkylene is defined herein. Representative carboxyalkyls include carboxymethyl and carboxyethyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like. The prefix spiro before cycloalkyl means that geminal substituents on a carbon atom are replaced to form 1,1-cycloalkyl. "Cycloalkylene" means a bivalent cycloalkyl having about 4 to about 8 carbon atoms. Preferred cycloalkylenyl groups include 1,2-, 1,3-, or 1,4-cis or trans-cyclohexylene.

"Cycloalkenyl" means a non-aromatic mono- or multicyclic ring system of about 3 to about 10 carbon atoms, preferably of about 5 to about 10 carbon atoms which contains at least one carbon-carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Cyanine dye" generically refers to a compound having two substituted or unsubstituted nitrogen-containing heterocyclic rings joined by an unsaturated bridge.

"Halo" or "halogen" mean fluoro, chloro, bromo, or iodo.

"Heteroaralkenyl" means a heteroaryl-alkenylene-group wherein heteroaryl and alkenylene are as defined herein. Preferred heteroaralkenyls contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene-group wherein heteroaryl and alkylene are as defined herein. Preferred heteroaralkyls contain a lower alkylene group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is as defined herein. A representative heteroaralkyloxy group is 4-pyridylmethyloxy.

"Heteroaralkynyl" means an heteroaryl-alkynylene- group wherein heteroaryl and alkynylene are as defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is as defined herein. Representative heteroaroyl groups include thiophenoyl, nicotinoyl, pyrrol-2-ylcarbonyl, pyridinoyl, and the like.

"Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroarylene" means an bivalent aromatic monocyclic or multicyclic ring system radical of about 5 to about 14 ring atoms, preferably about 5 to about 10 ring atoms, in which one or more of the atoms in the ring system is/are element(s) other than carbon, for example nitrogen, oxygen or sulfur. Preferred heteroarylenes contain about 5 to about 6 ring atoms. The "heteroarylene" is optionally substituted by one or more "ring system substituents" which may be the same or different, and are as defined herein.

"Heteroaryleneoxycarbonyl" means a heteroarylene-O—CO— group wherein heteroarylene is as defined herein.

"Heteroarylenecarbamoyl" means a heteroarylene-NH—CO— group wherein heteroarylene group is defined herein.

"Heteroarylenesufonylcarbamoyl" means a heteroarylene-$SO_2$—NH—CO— group wherein heteroarylene group is defined herein.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"Linking group" comprises the atoms joining the dye with the biomolecule. For example, with reference to Table 1, column A is a list of the reactive functionalities, which functionalities can be on the dye or the biomolecule. Column B is a list of the complementary groups, either on the biomolecule or the dye (preferably, a carboxyl, hydroxyl, thiol, or amino functionality), which together with the reactive functionalities form a resulting bond of column C. The linking group comprises the resulting bond, and optionally additional atoms. See also R. Haugland, Molecular Probes Handbook of Fluorescent Probes and Research Chemicals, Molecular probes, Inc. (1992). In one embodiment, $R^{18}$ represents a linking group before the attachment reaction occurs, $R^{30}$ represents the resultant attachment between the dye and the biomolecule. Preferred linking groups include phosphoramidite groups, NHS ester, activated carboxylic acid, thiocyanate, isothiocyanate, maleimide and iodoacetamide. As used herein, the term "activated carboxylic acid" is a derivative of a carboxyl group that is more susceptible to nucleophilic attack than a free carboxyl group; e.g., acid anhydrides, thioesters, acyl halides, NHS ester and sulfo NHS esters.

"Oxo" means a group of formula >C=O (i.e., a carbonyl group).

"Phosphoramidityl" means a trivalent phosphorous atom bonded to two —OR groups and a nitrogen atom wherein the nitrogen is optionally substituted.

"Ring system substituents" mean substituents attached to aromatic or non-aromatic ring systems inclusive of hydrogen, alkyl, aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, carboxyalkyl, heteroarylsulfinyl, alkylthio, arylthio, nitrile, $NO_2$ heteroarylthio, aralkylthio, heteroaralkylthio, cycloalkyl, cycloalkenyl, heterocyclyl, heterocyclenyl, aryidiazo, heteroaryldiazo, amidino, and the like.

"Sulfonato" is an $SO_3^-$ group, preferably to a cation.

"Sulfo-phenoxy dye" is a cyanine dye wherein the unsaturated bridge of the cyanine dye is substituted with an ether linkage to a benzene ring that is substituted with a sulfonato group, preferably in the 4 position on the benzene ring.

All other acronyms and abbreviations have the corresponding meaning as published in journals relative to the art of organic chemistry.

II. Preferred Cyanine Dyes

A preferred cyanine dye is a compound of the formula (I):

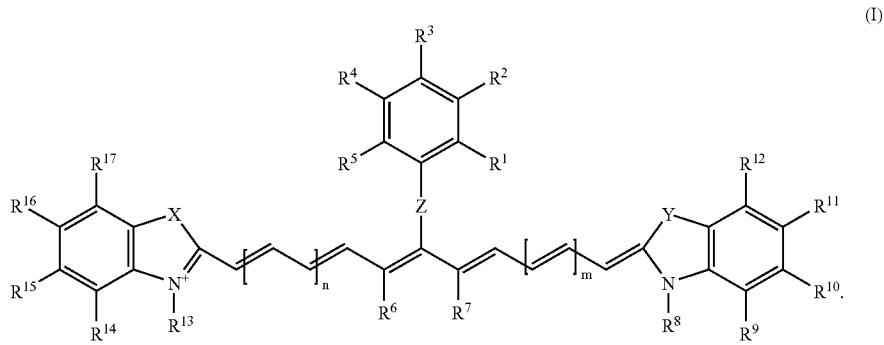

(I)

Preferably, Z is a heteroatom having at least one lone pair of electrons. In a particularly preferred embodiment, Z is O, S, or $NR^{35}$ wherein $R^{35}$ is H or alkyl. If $R^{35}$ is alkyl, it is preferred that $R^{35}$ is lower alkyl. Preferably, Z is of such a structure that only one atom is in the direct linkage between the benzene ring bonded to Z and to the polyene chain of the formula

bonded to Z. Side chains on the linkage between the benzene ring and the polyene chain are acceptable. In those embodiments having side chains, lower alkyl side chains are preferred.

$R^1$-$R^5$ are each independently H, alkyl, halo, carboxyl, amino, or $SO_3^-Cat^+$, wherein $Cat^+$ is a cation and at least one of $R^1$-$R^5$ is $SO_3^-Cat^+$. It is preferred that $R^3$ be $SO_3^-Cat^+$. It is particularly preferred that $Cat^+$ be $H^+$ or an alkali metal ion such as $Na^+$.

$R^6$ and $R^7$ are each H, alkyl, or optionally, together with

the group to which they are bonded, form a ring. It is preferred that $R^6$ and $R^7$ together with the atoms to which they are bonded form a ring. It is preferred that the ring have 4 to 10 member atoms, more preferably 5 or 6 member atoms. In one preferred embodiment, it is preferred that the ring including $R^6$ and $R^7$ be substituted, preferably with a sulfonato radical.

The integers m and n are each independently integers from 0 to 5. Preferably, both the sum of m and n are two. More preferably, the sum of m and n is one. Most preferably, both m and n are zero. As the sum of m and n rises, so too does the wavelength of the dye. Generally, the addition of each double bond in the polyene chain can increase the wavelength by about 40 to 120 nm. For the absorption changes accompanied with trimethine to pentamethine or pentamethine to heptamethine, there is a typically a bathochromic shift (red shift) of about 100 nm. For example, when m and n are both 0, the wavelength of the preferred dye is about 770 nm. When m and n are both 1, the wavelength of the preferred dye is about 950 nm. The most preferred dyes operate in the NIR spectrum (600-1000 nm).

X and Y are each independently O, S, Se, or $CR^{19}R^{20}$, wherein $R^{19}$ and $R^{20}$ are each independently alkyl, or optionally form a ring together with the carbon atom to which they are bonded. It is preferred that X and Y are a heteroatom such as O, S, and Se. When X or Y is $CR^{19}R^{20}$, it is preferred that both $R^{19}$ and $R^{20}$ are both lower alkyl, more preferably, both $R^{19}$ and $R^{20}$ are both methyl.

$R^8$ and $R^{13}$ are each independently alkyl, $(CH_2)_rR^{25}$ or $(CH_2)_rR^{18}$; wherein at least one of $R^8$ and $R^{13}$ is $(CH_2)_rB$ and wherein r is an integer from 1 to 50, and $R^{25}$ is a non-reactive functional group that does not directly react with a carboxyl, hydroxyl, amino, or a thiol group, and $R^{18}$ is a functional group that can react with a carboxyl, hydroxyl, amino, or thiol group. In a preferred embodiment, one of $R^8$ and $R^{13}$ is $(CH_2)_rR^{18}$ and the other is $(CH_2)_rR^{25}$. In other words, it is preferred that one of $R^8$ and $R^{13}$ react with the biomolecule to form a bond to that biomolecule, and that the other does not react. The $R^{18}$ group must be able to covalently bond with the biomolecule being labeled. Particularly preferred $R^{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. Particularly preferred $R^{25}$ groups include hydroxyl, thioacetyl, and sulfonato.

$R^9$-$R^{12}$ and $R^{14}$-$R^{17}$ are each independently H, alkyl, halo, amino, sulfonato, $R^{21}COOH$, $R^{21}OR^{22}$, $R^{21}SR^{22}$, or $R^{21}COOR^{22}$ wherein $R^{21}$ is a bond or alkylene and $R^{22}$ is alkyl, or optionally $R^{11}$ and $R^{12}$ together with the atoms to which they are bonded form an aromatic ring, or optionally $R^{16}$ and $R^{17}$ together with the atoms to which they are bonded form an aromatic ring. In one preferred embodiment, one or both of $R^{11}$ and $R^{16}$ is sulfonato. In another preferred embodiment, when $R^{11}$ and $R^{12}$ together with the atoms to which they are bonded form an aromatic ring, the ring is substituted in at least one position with a sulfonato group. In another preferred embodiment, when $R^{16}$ and $R^{17}$ together with the atoms to which they are bonded form an aromatic ring, the ring is substituted in at least one position with a sulfonato group, a halo group, an alkyl substituent, or an amino substituent.

Another preferred cyanine dye is of the formula (V):

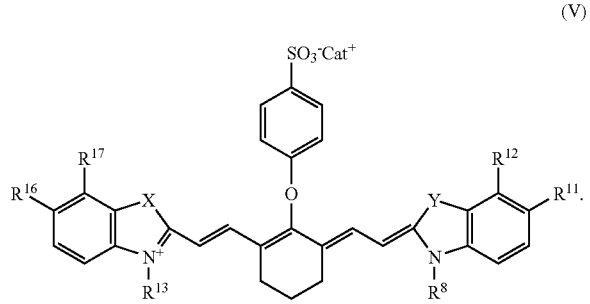

(V)

$Cat^+$ is a cation. Preferably, $Cat^+$ is $H^+$ or a metal ion. More preferably, $Cat^+$ is an alkali metal ion, most preferably $Na^+$. X and Y are each independently O, S, Se, or $(CH_3)_2C$.

$R^8$ and $R^{13}$ are each independently alkyl, $(CH_2)_rR^{25}$ or $(CH_2)_rR^{18}$; wherein at leas one of $R^8$ and $R^{13}$ is $(CH^2)_rR^{18}$ and wherein r is an integer from 1 to 50, and $R^{25}$ is a functional group that does not directly react with a carboxyl, hydroxyl, amino, or a thiol group, and $R^{18}$ is a functional group that can react with a carboxyl, hydroxyl, amino, or thiol group. In a preferred embodiment, one of $R^8$ and $R^{13}$ is $(CH_2)_rR^{18}$ and the other is $(CH_2)_rR^{25}$. In other words, it is preferred that one of $R^8$ and $R^{13}$ react with the biomolecule to form a bond to that biomolecule, and that the other does not react. The $R^{18}$ group must be able to covalently bond with the biomolecule being labeled. Particularly preferred $R^{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. Particularly preferred $R^{25}$ groups include hydroxyl, thioacetyl, and sulfonato.

$R^{11}$ and $R^{12}$ are either H, sulfonato, or together with the atoms to which they are bonded form an aromatic ring. In a preferred embodiment, $R^{11}$ is sulfonato. In another preferred embodiment, when $R^{11}$ and $R^{12}$ together with the atoms to which they are bonded form an aromatic ring, the ring is substituted in at least one position with a sulfonato group.

$R^{16}$ and $R^{17}$ are either H, sulfonato, or together with the atoms to which they are bonded form an aromatic ring. In a preferred embodiment, $R^{16}$ is sulfonato. In another preferred embodiment, when $R^{16}$ and $R^{17}$ together with the atoms to which they are bonded form an aromatic ring, the ring is substituted in at least one position with a sulfonato group.

The preferred cyanine dyes can be excited efficiently by commercially available equipment purchasable through companies such as LI-COR, Toshiba, Phillips, Blue Sky Research, and NEC.

The preferred cyanine dyes have sufficient solubility in aqueous solutions that once they are attached to a soluble biomolecule, the biomolecule retains its solubility. The preferred dyes also have good solubility in organic media, which provides considerable versatility in synthetic approaches to the labeling of desired biomolecules.

The preferred cyanine dyes have increased chemical stability in the presence of ammonium hydroxide and DTT. The preferred cyanine dyes have improved photostability and thermostability over existing phenoxy cyanine dyes.

III. Preparing the Cyanine Dyes

The preferred cyanine dyes are prepared using methods that are well known in the art. Generally, cyanine dyes are prepared according to the procedures taught in Hamer, F. M., *Cyanine Dyes and Related Compounds*, Weissberger, Mass., ed. Wiley Interscience, N.Y. 1964. Further, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

One common synthesis route involves preparing substituted or unsubstituted indolesulfonate quaternary salts according to procedures that are well known in the art, some of which are detailed in the examples of this specification. Particularly preferred indole quaternary salts include, among others, indolesulfonate quaternary salt and benzindole alcohol quaternary salt, which are exemplified in this specification.

The pair of synthesized salts are then reacted with a commercially available (through ALDRICH) Schiffs base such as N-[(3-(Anilinomethylene)-2-chloro-1-cyclohexen-1-yl)methylene]aniline monohydrochloride using techniques and reaction conditions that are well known in the art, some of which are detailed in the examples of this specification. The product is then reacted with a hydroxybenzene sulfonic acid to give a dye according the present invention. The dye can be further modified to give other dyes according to the present invention, for example, by reacting the dye with commercially available phosphoramidites such as 2-cyanoethyl tetraisopropylphosphorodiamidite using techniques and reaction conditions that are well known in the art, some of which are detailed in the examples of this specification.

IV. Labeling Biomolecules

The cyanine dyes of the present invention can be attached to biomolecules, which are defined above. Through linking groups, the cyanine dye can be linked to the biomolecule, for example, by using phosphoramidite chemistry, ultimately forming a phosphate linkage between the dye and the biomolecule. For examples of such labeling methods, see U.S. Pat. No. 6,027,709, which discloses many preferred linking groups, linking methods, and biomolecules that can be readily labeled. It is generally preferred to prepare a phosphoramidite of a cyanine dye to label DNA molecules in a DNA synthesis machine. It is preferred to attach the dye to the 5' end of a protected, support-bonded oligonucleotide through standard phosphoramidite chemistry. Synthesis at the 200 nmole scale produces typical crude yields of dye labeled oligonucleotides of 50-60 nmole.

Many methods of linking dyes to various types of biomolecules are well known in the art. For a through review of oligonucleotide labeling procedures, see R. Haugland in Excited States of Biopolymers, Steiner ed., Plenum Press (1983), Fluorogenic Probe Design and Synthesis: A Technical Guide, P E Applied Biosystems (1996), and G. T. Herman, Bioconjugate Techniques, Academic Press (1996).

It is preferred that antibody labeling is carried out in a buffer optionally including an organic co-solvent, under basic pH conditions, and at room temperature. It is also preferred that the labeled antibody be purified by gel permeation chromatography using equipment such as a SEPHADEX G-50 column to remove unconjugated dye, or dialysis. Those of skill in the art will know of other ways and means for purification.

In a preferred embodiment method of labeling a biomolecule, the $R^{18}$ group of either the $R^8$ or the $R^{13}$ group of any of the preferred cyanine dyes reacts with a thiol, a hydroxyl, a carboxyl, or an amino group on a biomolecule, forming an attachment ($R^{30}$) between the dye and the biomolecule. Typically, this reaction is carried out in mixtures of aqueous buffer and an organic solvent such as DMF at pH 8 to 9. In one preferred embodiment, using phosphoramidite chemistry, solid phase synthesis is preferred, as disclosed in U.S. Pat. No. 6,027,709.

Biomolecules can be labeled according to the present invention using a kit. In a preferred embodiment of a kit, the kit comprises a dye of either formula (I) or (V), and a buffer. Preferably, the kit contains a coupling buffer such as 1 M $KH_2PO_4$ (pH 7.0). Preferably, the buffer has a qualified low fluorescence background.

Optionally, the kit can contain a purification sub-kit. After labeling a biomolecule with one of the preferred dyes, the labeled biomolecule may be separated from any side reaction products and any free hydrolyzed product resulting from normal hydrolysis. For biomolecules containing 13 or fewer amino acids, preparative thin layer chromatography (TLC) can remove impurities. Invitrogen supplies a TLC Peptide Purification Kit, which is specially designed to purify dye-labeled peptides or proteins.

For larger biomolecules such as larger peptides or proteins, a SEPHADEX G-15 or G-25 resin may remove unwanted derivatives. Invitrogen supplies a Gel Filtration of Proteins Kit, which is designed to separate dye-labeled peptides and proteins from free dye. The dye-labeled biomolecules that remain after desalting can often be used successfully without further purification. In some cases, it may be necessary to resolve and assess the activity of the different dye products using HPLC or other chromatographic techniques.

Once labeled, one preferred dye-labeled biomolecule is of the formula (XV):

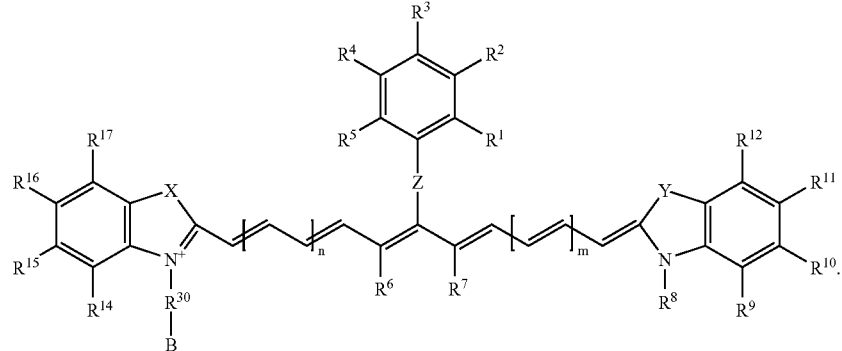

All of the substituents are defined as above. B is a biomolecule and $R^{30}$ is $(CH_2)_rL$ wherein r is an integer from 1 to 50, and L is a linking group. Preferably, B is a protein, a peptide, an enzyme substrate, a hormone, an antibody, an antigen, a hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA. For a list of preferred label terminators for use in DNA sequencing, see U.S. Pat. No. 5,332,666, herein incorporated by reference.

Preferably, r ranges from 1 to 5. Preferably, L is phosphoramidityl or other linkage group, some of which are exemplified in U.S. Pat. No. 6,027,709. In one preferred embodiment, L is a diphosphate ester amidite.

Another preferred dye-labeled biomolecule is of the formula (XX):

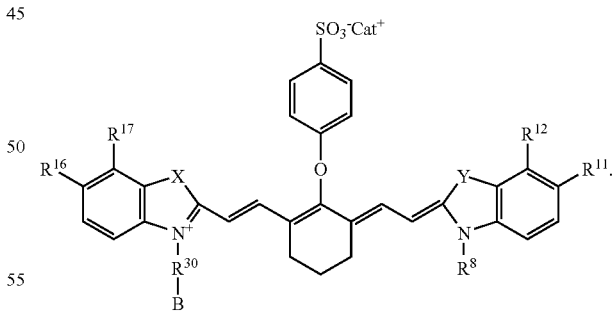

All of the substituents are defined as above. B is a biomolecule and $R^{30}$ is $(CH_2)_rL$ wherein r is an integer from 1 to 50, and L is a linking group. Preferably, r ranges from 1 to 5. In one preferred embodiment, when the linkage is formed, L is a phosphate diester. Examples of similar preferred embodiments are disclosed in U.S. Pat. No. 6,027,709.

DNA Sequencing

The dye-labeled biomolecules of the present invention can be used in biological applications such as DNA sequencing.

The labeled biomolecule such as an oligonucleotide can be used, for example, as a primer in the Sanger method of DNA sequencing, as a tailed primer for genotyping or as a hybridization probe. Certain well-known techniques and reaction conditions for DNA sequencing are detailed in the examples of this specification.

Well-known methods of DNA sequencing include the Maxam-Gilbert chemical degradation method, described in Maxam et al., Meth. in Enzym. 65:499 (1980), and the Sanger dideoxy chain termination technique, described in Sanger et al., P.N.A.S. USA 74:5463 (1977). In each method DNA fragments labeled with $^{32}$P are generated which are analyzed by gel electrophoresis. Radio-labeled phosphorus is not commonly used in these methods anymore; dyes have taken its place.

DNA sequencing is also summarized in review articles. See, e.g., Middendorf, L. R., Humphrey, P. G., Narayanan, N., and Roemer, R. C. "Sequencing Technology" in: Biotechnology. Rehm, H.-J. and Reed, G. (Editors), Wiley-VCH Publishers, Germany—(Chapter—submitted); B. Barrell, The FASEB Journal, 5, 40 (1991); and G. L. Trainor, Anal. Chem. 62, 418 (1990), and references cited therein. The most widely used DNA sequencing chemistry is the enzymatic chain termination method of Sanger, mentioned above, which has been adopted for several different sequencing strategies. The sequencing reactions are either performed in solution with the use of different DNA polymerases, such as the thermophilic Taq DNA polymerase [M. A. Innes, Proc. Natl. Acad. Sci. USA, 85: 9436 (1988)] or specially modified T7 DNA polymerase ("SEQUENASE") [S. Tabor and C. C. Richardson, Proc. Natl. Acad. Sci. USA, 84, 4767 (1987)], or in conjunction with the use of polymer supports. See for example S. Stahl et al., Nucleic Acids Res., 16, 3025 (1988); M. Uhlen, PCT Application WO 89/09282; Cocuzza et al., PCT Application WO 91/11533; and Jones et al., PCT Application WO 92/03575, incorporated by reference herein.

In certain embodiments, the present invention provides a compound of the formula XXI:

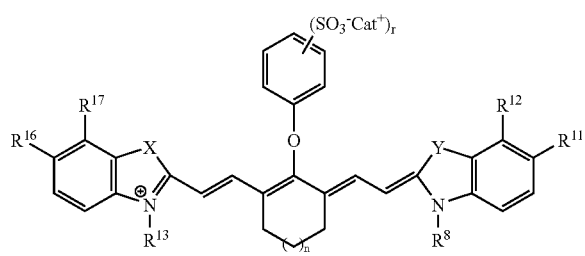

wherein Cat$^+$ is a cation; r is an integer equal to 1, 2, or 3; X and Y are each independently O, S, Se, or (CH$_3$)$_2$C; and R$^8$ and R$^{13}$ are each independently alkyl, L—R$^{25}$ or L—R$^{18}$; wherein at least one of R$^8$ and R$^{13}$ is L—B; R$^{25}$ is a non-reactive functional group that does not directly react with a carboxyl, hydroxyl, amino, or a thiol group; L is a linker; B is a ligand; n is 0, 1, 2 or 3; R$^{11}$ and R$^{12}$ are each independently F, H, sulfonato, or together with the atoms to which they are bonded form an aromatic ring; and R 16 and R$^{17}$ are each independently F, H, sulfonato, or together with the atoms to which they are bonded form an aromatic ring. Preferably, X and Y are (CH$_3$)$_2$C. Preferably, r is 1.

A wide range of non-reactive functional groups are suitable for R$^{25}$. Suitable groups include for example, hydroxyl, thioacetyl, sulfonato, optionally substituted alkyl, optionally substituted aryl, optionally substituted heteroaryl, optionally substituted unactivated carboxyl, optionally substituted cycloalkyl, and optionally substituted heterocyclyl, optionally substituted sulphates, optionally substituted phosphates, and optionally substituted ammonium salts.

In certain preferred aspects, R$^{11}$ and R$^{12}$ are each independently F, H, or sulfonato; R$^{16}$ and R$^{17}$ are each independently F, H, or sulfonato; and n is 1. Preferably, Cat$^+$ is H$^+$ or a metal ion. In certain aspects, at least one of X and Y is (CH$_3$)$_2$C. In order to achieve charge neutrality, a skilled person will understand that after the first additional "sufonato" group from R$^{11}$, R$^{12}$, R$^{16}$ and R$^{17}$ a Cat$^+$ is added. The first "sufonato" group is neutralized from the quaternary nitrogen r is preferably equal to 1.

In certain aspects, L is a member selected from the group of a direct link, or a covalent linkage, wherein the covalent linkage is linear or branched, cyclic or heterocyclic, saturated or unsaturated, having 1-60 atoms selected from the group consisting of C, N, P, O, and S, wherein L can have additional hydrogen atoms to fill valences, wherein the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

In yet other aspects, L is a member selected from the group of a PEG, a block copolymer of PEG-polyurethane and a PEG-polypropylene. In still yet other aspects, L is a member selected from the group of a polysaccharide, a polypeptide, an oligosaccharide, a polymer, a co-polymer and an oligonucleotide.

In certain preferred aspects, L is of the formula:

—X$^1$—Y$^1$—X$^2$— wherein: X$^1$ is a member selected from the group of a bivalent radical, a direct link, oxygen, an optionally substituted nitrogen and sulfur; Y$^1$ is a member selected from the group of a direct link and C$_1$-C$_{10}$ alkylene optionally interrupted by a heteroatom; and X$^2$ is a member selected from the group of a bivalent radical, a direct link, oxygen, an optionally substituted nitrogen and sulfur.

Preferably, the bivalent radical of X$^1$ and X$^2$ are each independently selected from the group of a direct link, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

In certain preferred aspects, L is —(CH$_2$)$_r$—, wherein r is an integer from 1 to 50. For example, both R$^8$ and R$^{13}$ are (CH$_2$)$_r$B, wherein r is an integer from 1 to 5. Preferably, R$^{25}$ is an optionally substituted alkyl group.

In certain preferred aspects, the compound has the structure of:

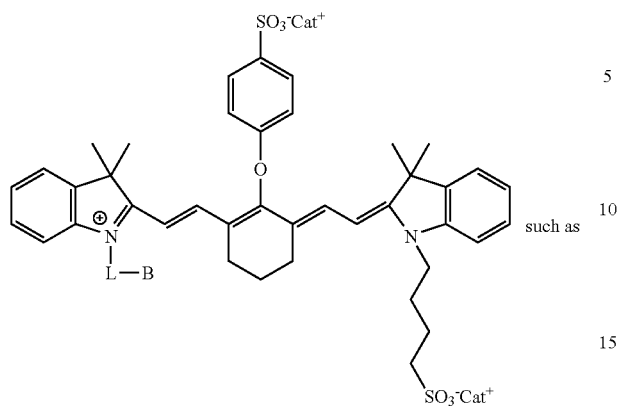
such as
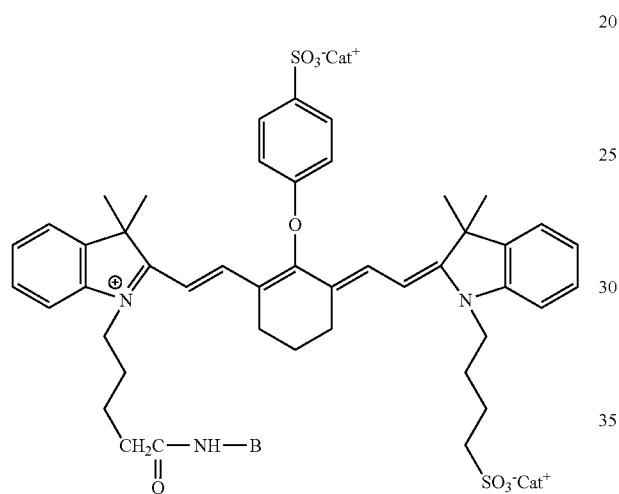
or the structure of:
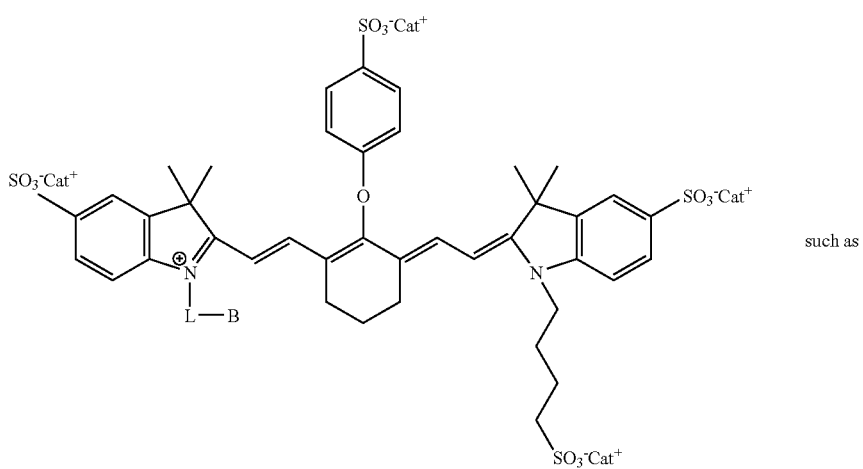
such as

-continued
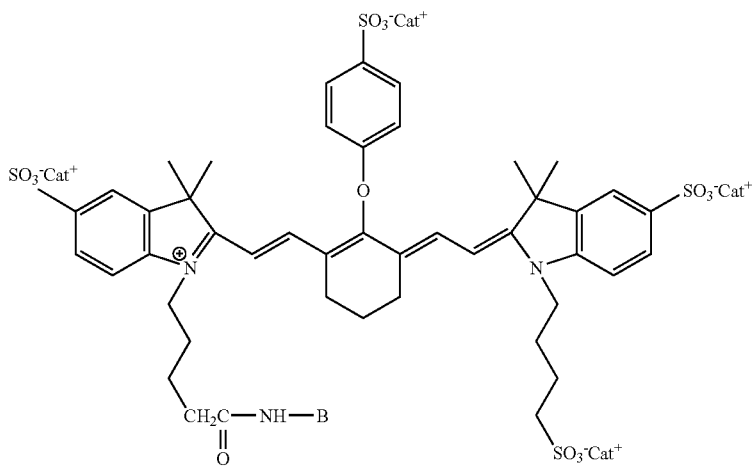
or
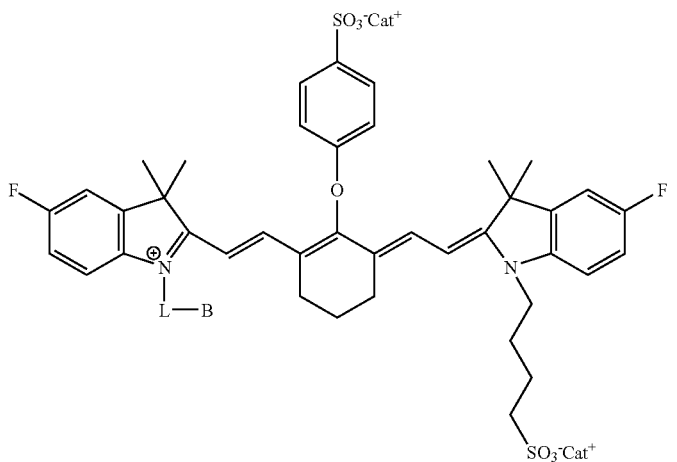
such as
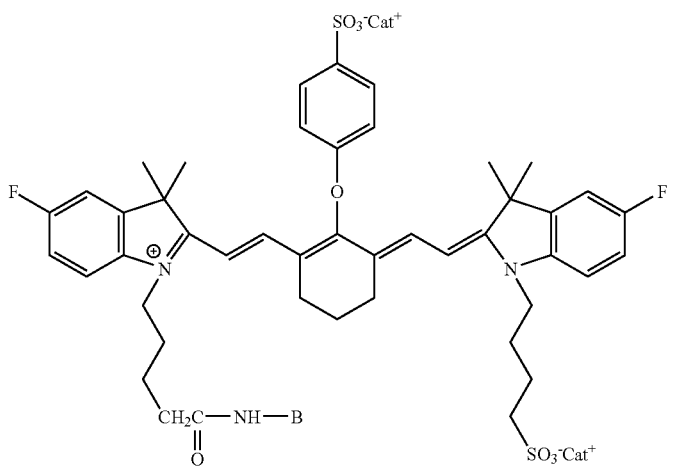
or

-continued
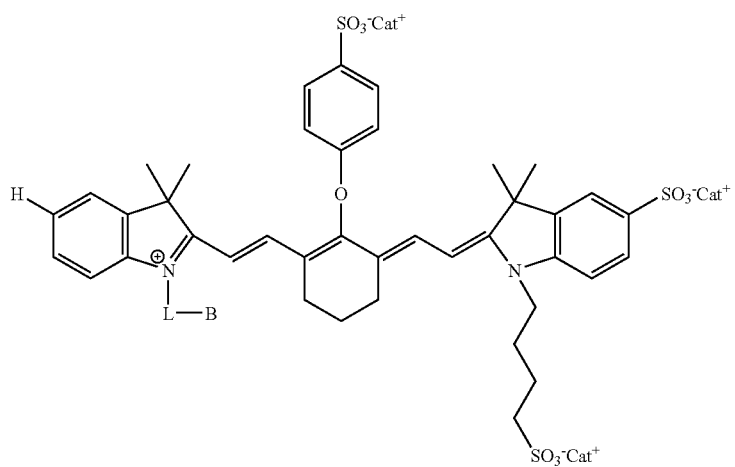
such as
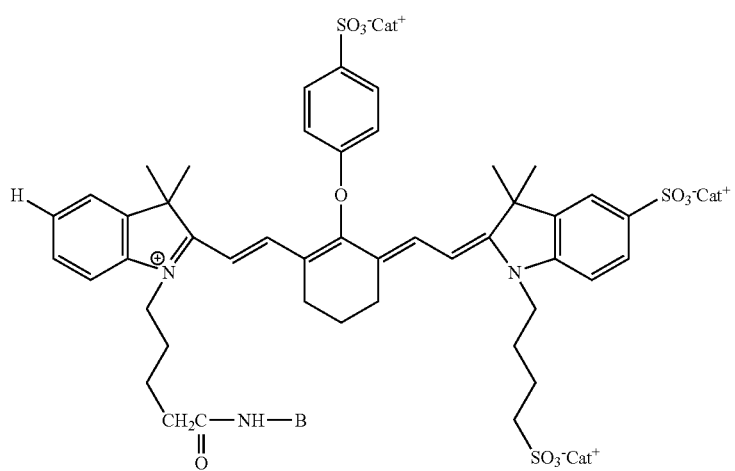
or
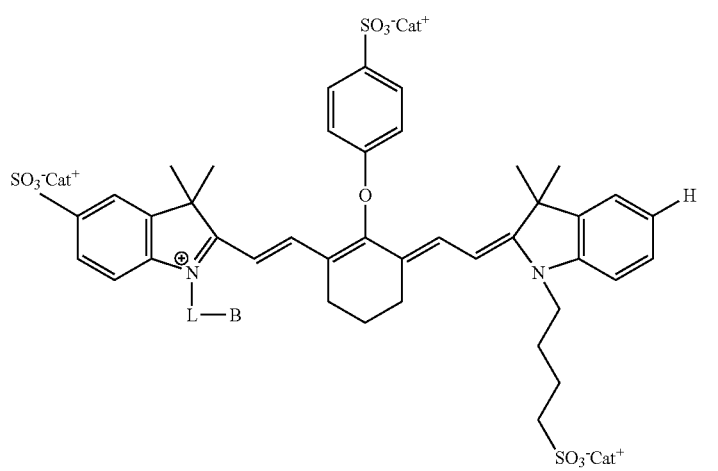
such as

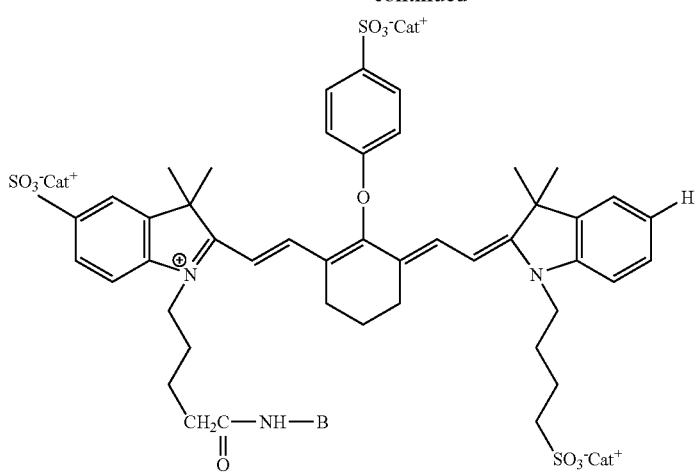
or
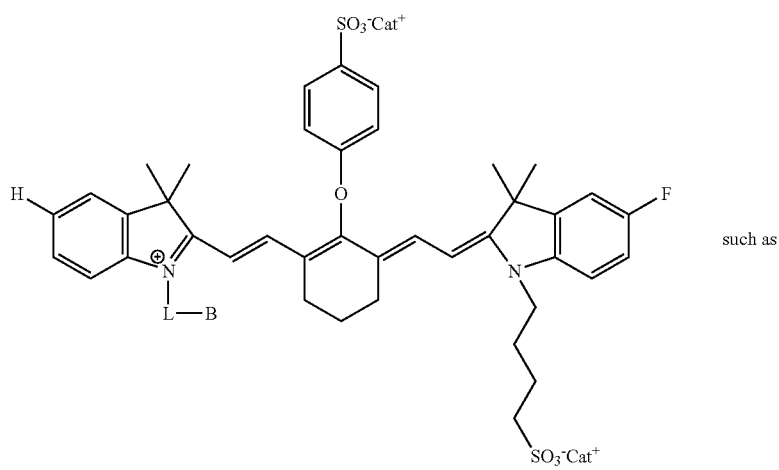
such as
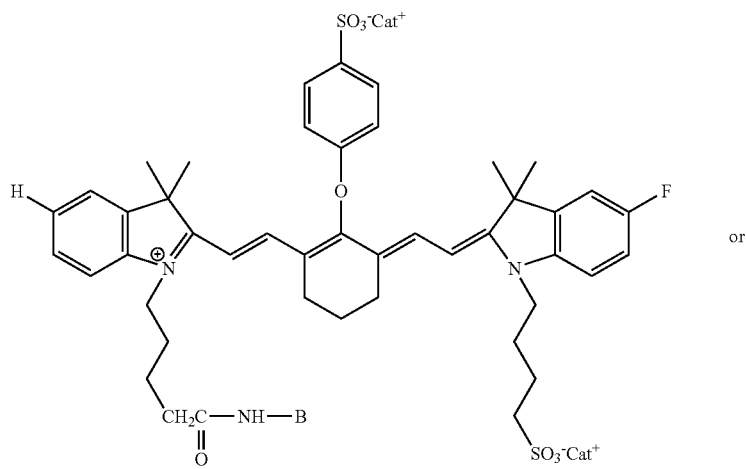
or

-continued
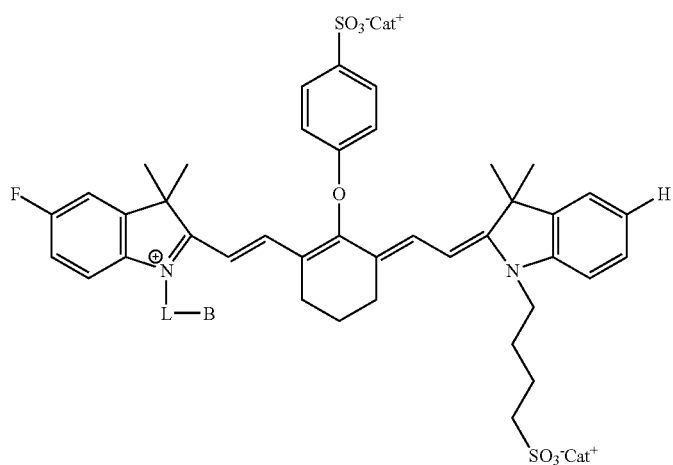
such as
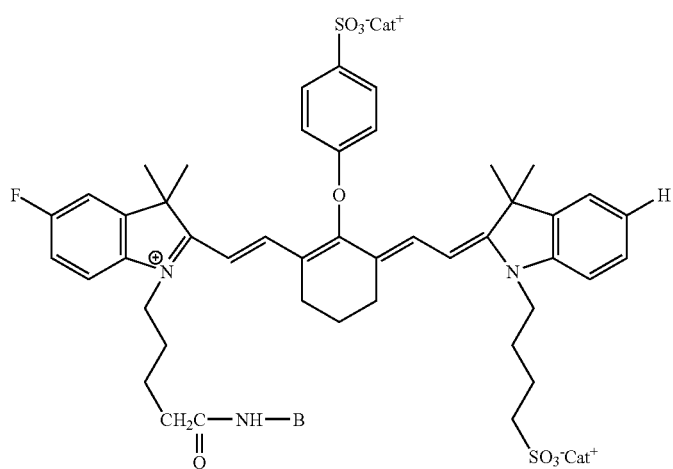
or
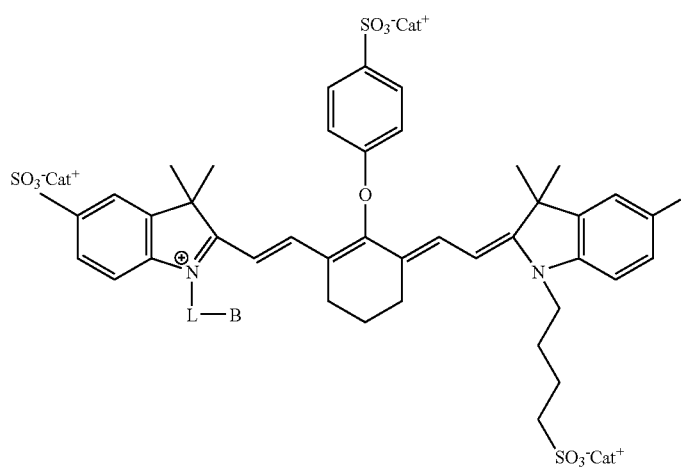
such as

-continued
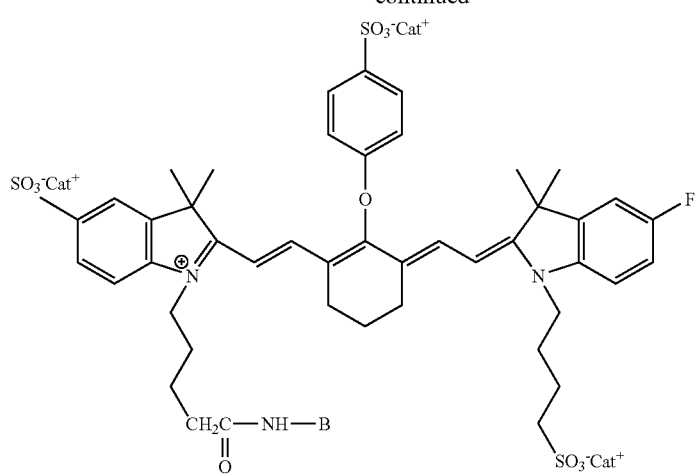
or
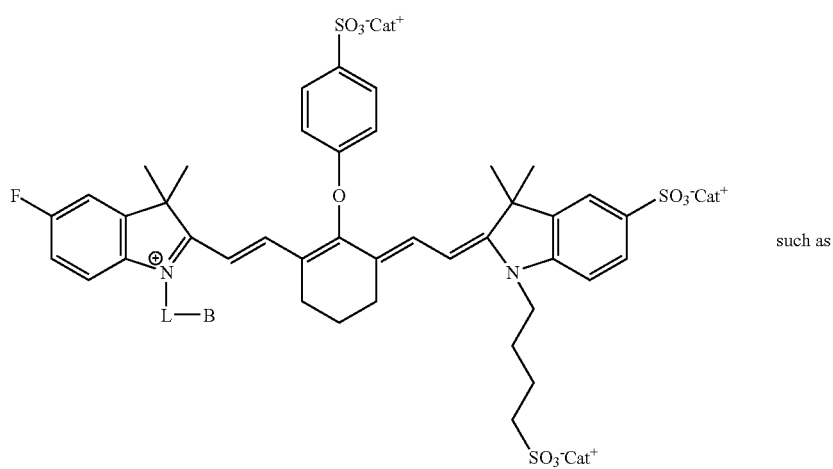
such as
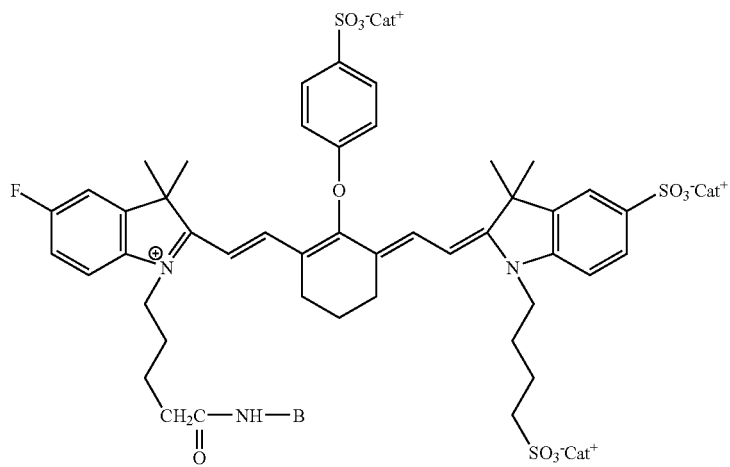

In certain preferred aspects, B is a ligand that has affinity for a receptor selected from the group consisting of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocordicosteroid receptor, Retinoid-X receptor, RHAMM, high affinity folate receptors, Met receptor, estrogen receptor and Ki67.

Alternatively, B is selected from the group of somatostatin, endostatin, a carbohydrate, a monosaccharide, a disaccharide, a trisaccharide, an oligosaccharide, aptamer, liposome and PEG.

In certain other embodiments, B is 2-deoxy-D-glucose, 2-deoxy-D-glucosamine, a glucose derivative, glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, and tagatose.

In still other aspects, B is selected from the group of angiopoietins, angiostatin, angiotensin II, $\alpha_2$-antiplasmin, annexin V, β-cyclodextrin tetradecasulfate, endoglin, endosialin, endostatin, epidermal growth factor, fibrin, fibrinopeptide β, fibroblast growth factor, FGF-3, basic fibronectin, fumagillin heparin, hepatocyte growth factor, hyaluronan, insulin-like growth factor, interferon-$\alpha,\beta$ inhibitors, IL inhibitor, laminin, leukemia inhibitory factor, linomide, matrix metalloproteinase-2, metalloproteinases, metalloproteinase inhibitors, antibodies or fragments, monoclonal antibodies or fragments, cyclic $RGD_D$ FV, placental growth factor, placental proliferin-related protein, plasminogen, plasminogen activator, plasminogen activator inhibitor-1, platelet activating factor antagonists, platelet-derived growth factor, platelet-derived growth factor receptors, platelet-derived endothelial cell growth factor, pleiotropin, proliferin, proliferin-related protein, selectins: E-selectin, SPARC, (secreted protein acidic and rich in cysteine) snake venoms, substance P, suramin, tissue inhibitor of metalloproteinases, thalidomide, thrombin, thrombin-receptor-activating tetradecapeptide, transforming growth factor-$\alpha,\beta$, transforming growth factor receptor, tumor growth factor-$\alpha$, tumor necrosis factor, vitronectin, avidin and streptavidin.

In certain preferred aspects, B is epidermal growth factor. In other aspects, B is a moiety that has affinity or can be incorporated into bone, such as calcein and calcein derivatives.

Selected examples of reactive functionalities useful for the attaching the dye to the ligand or biomolecule are shown in Table 1, wherein the bond results from the reaction of a dye with a ligand or biomolecule. Those of skill in the art will know of other bonds suitable for use in the present invention.

TABLE 1

| A<br>Reactive functionality<br>(either on the dye or<br>the biomolecule). | B<br>Complementary group<br>(either on the bio-<br>molecule or the dye). | C<br>The resulting<br>bond (e.g., $R^{30}$) |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| activated carboxylic acids | amines/anilines | carboxamides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —COM, where M is a good leaving group (e.g. succinimidyloxy (—OC$_4$H$_4$O$_2$) sulfosuccinimidyloxy (—OC$_4$H$_3$O$_2$SO$_3$H), -1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or OCN-R$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

When linking a dye having a carboxylic acid, with an amine-containing ligand or biomolecule, the dye carboxylic acid can first be converted to a more reactive form using an activating reagent, to form for example, a N-hydroxy succinimide (NHS) ester or a mixed anhydride. The amine-containing ligand or biomolecule is treated with the resulting activated acid to form an amide linkage. Typically, this reaction is carried out in aqueous buffer optional co-solvent with DMSO or DMF at pH 8 to 9.

Similarly, the attachment of an isothiocyanate containing dye is analogous to the procedure for the carboxy dye, but no activation step is required. The amine-containing ligand or biomolecule is treated directly with the NCS dye to form a thiourea linkage. Typically, the reaction is carried out in aqueous buffer with an optional co-solvent with DMSO or DMF at pH 9 to 10.

If the dye compound has a reactive hydroxyl group, it can be linked to a ligand or biomolecule, such as DNA or RNA, through phosphoramidite chemistry. Use of the phosphoramidite allows labeling of the DNA or RNA during the synthesis process. The protected nucleotide is labeled while attached to a solid phase support. The free 5'-OH group is reacted with the phosphoramidite and a tetrazole activator to form a phosphite linkage which subsequently is oxidized to phosphate. The labeled DNA or RNA then is cleaved from the solid phase using ammonia or other standardized procedure.

In one aspect, the dyes of this invention have sufficient solubility in aqueous solutions that once they are attached to a soluble ligand or biomolecule, the ligand or biomolecule retains its solubility. They also have good solubility in organic media (e.g., DMSO or DMF), which provides considerable versatility in synthetic approaches to the labeling of desired materials.

In one embodiment, the present invention provides a method or process for making a dye-labeled ligand or biomolecule, the method comprising: contacting a ligand or biomolecule with a compound having Formula Ia to generate the compound of Formula If.

Biomolecules can be labeled according to the present invention using a kit. In one embodiment, the kit comprises a compound of Formula I and instructions for use. In a preferred embodiment, the kit further comprises a buffer. Preferably, the kit contains a coupling buffer such as 0.2 M $NaHCO_3/Na_2CO_3$. Preferably, the buffer has a qualified low fluorescence background.

In certain preferred aspects, the covalent linkage between L and B is selected from the group consisting of a direct bond, an amide bond, an ester bond, an ether bond, an oxime bond, a phosphate ester bond, a sulfonamide bond, a thioether bond, a thiourea bond, and an urea bond.

V. Additional Applications

In certain other aspects, the dye compounds of the present invention are used as in vivo optical imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. In one embodiment, the dye compounds of the invention are useful for the detection of the presence of tumors and other abnormalities by monitoring the blood clearance profile of the dyes. In another embodiment of the invention, the dye compounds are useful for laser assisted guided surgery for the detection of micro-metastases of tumors upon laparoscopy. In yet another embodiment, the dye compounds are useful in the diagnosis of atherosclerotic plaques and blood clots.

In further embodiments, the dye compounds of the present invention are used in the imaging of: (1) ocular diseases in ophthalmology, for example, to enhance visualization of chorioretinal diseases, such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; (5) breast tumors via 2D- or 3D-image reconstruction; and (6) brain tumors, perfusion, and stroke via 2D- or 3D-image reconstruction.

The compounds of the invention that are dye conjugates are particularly useful for imaging tumors, tissues, and organs in a subject. For example, the existence of cancer cells or cancer tissues can be verified by labeling an anti-tumor antibody with a dye compound of the present invention and then administering the dye-conjugated antibody to the subject for detection and imaging of the tumor. Conjugates between the dye compound and other antibodies, peptides, polypeptides, proteins, ligands for cell surface receptors, small molecules, and the like are also useful agents for the in vivo imaging of tumors, tissues, and organs in a subject.

The compounds of the invention may be administered either systemically or locally to the organ or tissue to be imaged, prior to the imaging procedure. In one embodiment, the compounds are administered intravenously. In another embodiment, the compounds are administered parenterally. In yet another embodiment, the compounds are administered enterally. The compositions used for administration of the compound typically contain an effective amount of the dye compound or conjugate along with conventional pharmaceutical carriers and excipients appropriate for the type of administration contemplated. For example, parenteral formulations advantageously contain a sterile aqueous solution or suspension of the dye compound or conjugate according to the invention. Compositions for enteral administration typically contain an effective amount of the dye in aqueous solution or suspension that may optionally include buffers, surfactants, thixotropic agents, flavoring agents, and the like.

The compositions are administered in doses effective to achieve the desired optical image of a tumor, tissue, or organ. Such doses may vary widely, depending upon the particular dye compound or conjugate employed, the tumor, tissue, or organ subjected to the imaging procedure, the imaging equipment being used, and the like.

The method of the present invention provides for administering to the subject a therapeutically effective amount of a dye compound; a targeting agent, such as a dye conjugate; or mixtures thereof. In one embodiment, the targeting agent selectively binds to the target tissue. Light at a wavelength or waveband corresponding to that which is absorbed by the photosensitizing agent is then administered. In another embodiment, the compounds of the present invention act agents capable of binding to one or more types of target cells or tissues, when exposed to light of an appropriate waveband, absorb the light, causing substances to be produced that illuminate, impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

In yet another embodiment, the compounds of the present invention are administered by any means known, including, but not limited to, ingestion, injection, transcutaneous administration, transdermal administration, and transillumination. Preferably, the compounds are administered transcutaneously to a subject. For example, "transcutaneous" as used herein refers to the passage of light through unbroken tissue. Where the tissue layer is skin or dermis, transcutaneous includes "transdermal" and it will be understood that the light source is external to the outer skin layer. However, the term "transillumination" as used herein refers to the passage of light through a tissue layer, such as the outer surface layer of an organ, e.g., the liver, and it will be apparent that the light source is external to the organ, but internal or implanted within the subject or patient.

In further embodiments of the invention, the target tumor, tissue, or organ for treatment is selected from the group consisting of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, neuronal tissue or diseased neuronal tissue, and diseased cells in which the disease is one of an autoimmune and an inflammatory disease. In yet a further embodiment, the target tissue is a lesion in the vascular system of a type selected from the group consisting of atherosclerotic lesions, arteriovenous malformations, aneurysms, and venous lesions.

In still further embodiments, the forms of energy include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Dyes typically have one or more absorption wavebands that excite them to produce the substances which illuminate, damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins.

In other aspects, the present invention provides a method for generating an image of a subject, said method comprising: administering a compound of formula XXI:

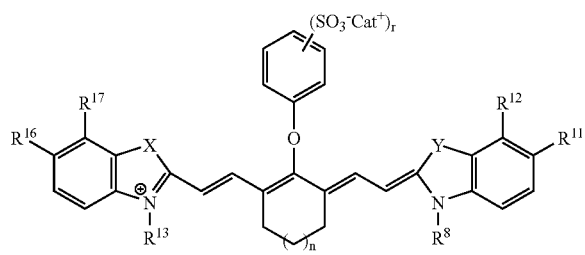

to the subject; and generating an image of said subject, wherein said compound has been distributed. In certain aspects, compound has been distributed to a tumor, to bone, to a tissue or an organ. The subject can be a human.

In certain aspects, the dye compounds of the present invention are used to directly stain or label a sample so that the sample can be identified or quantitated. For instance, such dyes can be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but ranges of 0.00001 mM up to 0.1 mM, such as about 0.001 to about 0.01 are possible. The optimal concentration is determined by systematic variation until satisfactory results with minimal background fluorescence is accomplished.

The dye compounds are most advantageously used to stain samples with biological components. The sample can comprise heterogeneous mixtures of components (e.g., including intact cells, fixed cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the concentrations of use.

The dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are excitable at or near the wavelengths 633-636 nm, 647 nm, 660 nm, 680 nm and beyond 700 nm, such as 780 nm, 810 nm and 850 nm as these regions closely match the output of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

EXAMPLES

The following section shows one of the preferred syntheses for making various compounds made according to the present invention, as well as experimental data for particular compounds. This section also provides examples for using the compounds made according to the present invention. The examples are intended to be illustrative, not limiting.

Example 1

Synthesizing an Intermediate Cyanine Dye

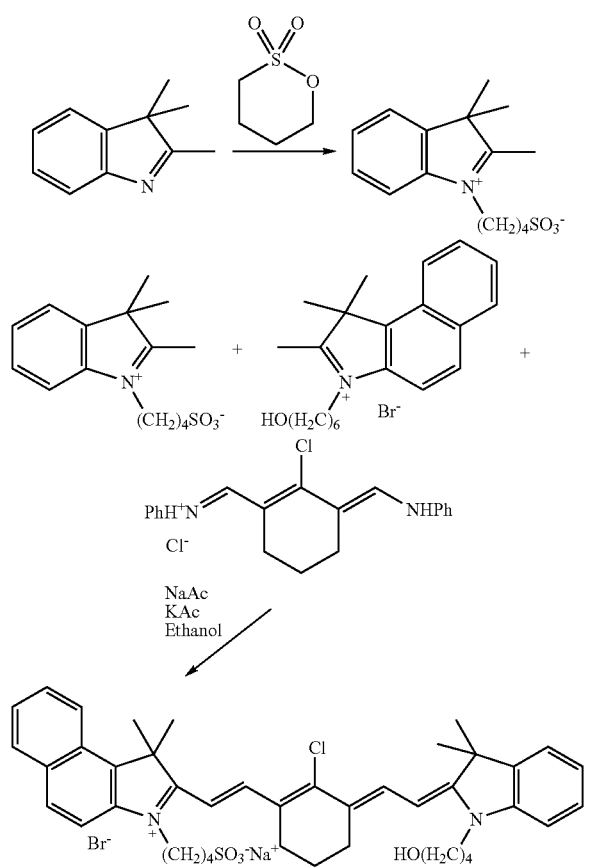

Step A: synthesis of indolesulfonate quaternary salt: A mixture of 160 g (1000 mmol) of 1,1,2-trimethyl-1H-indole (ALDRICH) and 340.4 g (256 ml; 2500 mmol; ALDRICH) of butanesultone was heated at 125° C. in 1 L RB flask with 400 ml of dichlorobenzene under the nitrogen atmosphere. After 16 h, the reaction was stopped and cooled to room temperature. The solid crystallizing out of the reaction mixture was filtered, then washed with ether (150 ml). The solid so obtained was dissolved in minimum volume of methanol (300 ml) and then precipitated by the addition of acetone (1600 ml). The solid was filtered and washed with acetone (150 ml×2). It was dried under vacuum to give 261.3 g (88.5%) of the quaternary salt. It was pure enough to use for the next step.

Step B: synthesis of benzindole alcohol quaternary salt: The quaternary salt was prepared according to the procedure of U.S. Pat. No. 6,027,709. In this case, 92.0 g of 1,1,2-Trimethyl-1H-benzindole (ACROS) was used, giving 113.0 g (60% yield) of pure benzindole alcohol quaternary salt.

Step C: synthesis of the chloro dye: A mixture containing benzindole alcohol quaternary salt (39 g; 100 mmol), indole-sulfonate quaternary salt (20.5 g; 100 mmol), in ethanol (400 ml) was stirred under nitrogen for 10 to 15 min. to obtain the uniform solution. To this solution was then added Schiffs base (35.9 g; 100 mmol; ALDRICH) followed by the addition of 100 ml of ethanol. The dark red colored solution was heated to 60° C. At this temperature, sodium acetate (21.32 g; 130 mmol) was added, followed by 12.80 g of potassium acetate (130 mmol). Temperature was raised to obtain vigorous reflux (110 to 115° C.) and maintained at this reflux for 35 to 40 min. Reaction was stopped and cooled to room temperature. The reaction mixture was poured into an ice bath (1 L) when an oily product formed and settled to the bottom. Water was decanted and the procedure was repeated until the water washings were clear. The oily product was triturated with ether (150 ml×3) and then with ethyl acetate (150 ml×3). The partially solidified product was dissolved in methanol (350 ml) and methanol was subsequently removed by evaporation on rotary evaporator. The solid dye was dried under vacuum. It was further purified by column chromatography (silica gel 60, 35-75 mm; solvent gradient 10% methanol in acetonitrile to 30% methanol in acetonitrile) to give a pure chloro dye (29.0 g; Yield 40%).

Example 2

Synthesizing a Cyanine Dye

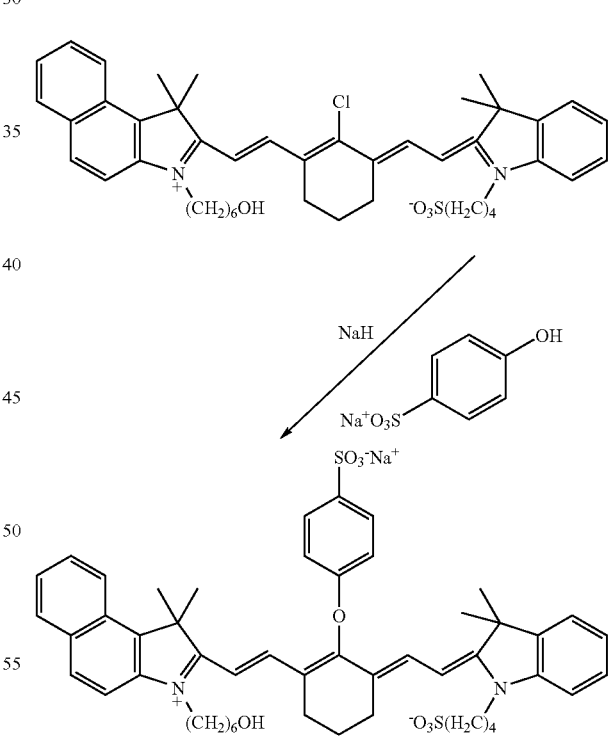

Synthesis of sulfo-phenoxy dye: In 40 ml of dry DMF was dissolved 2.95 g (12.70 mmol) of 4-hydroxybenzenesulfonic acid. After adding 1.08 g (60%; 26.8 mmol) of sodium hydride, the mix was stirred at room temperature for 10 min. under nitrogen. The chloro dye of Example 1 (7.41 g; 10 mmol), dissolved in 25 ml of dry DMF was added to the reaction mixture and stirred further for 45 to 50 min. Absorption max of 788 nm at the end of this period indicated an hypochromic shift of 13 nm (chloro dye abs. at 801 nm), and thus the formation of the sulfo-phenoxy dye. Dry ice was added to the reaction mixture and DMF was removed under vacuum. The crude dye was purified by column chromatography (silica gel 60; solvent gradient: 10% methanol in acetonitrile to 30% methanol in acetonitrile) to obtain 4 g of the pure dye. (Yield 45%).

Example 3

Synthesizing a Sulfo-Phenoxy Phosphoramidite Cyanine Dye

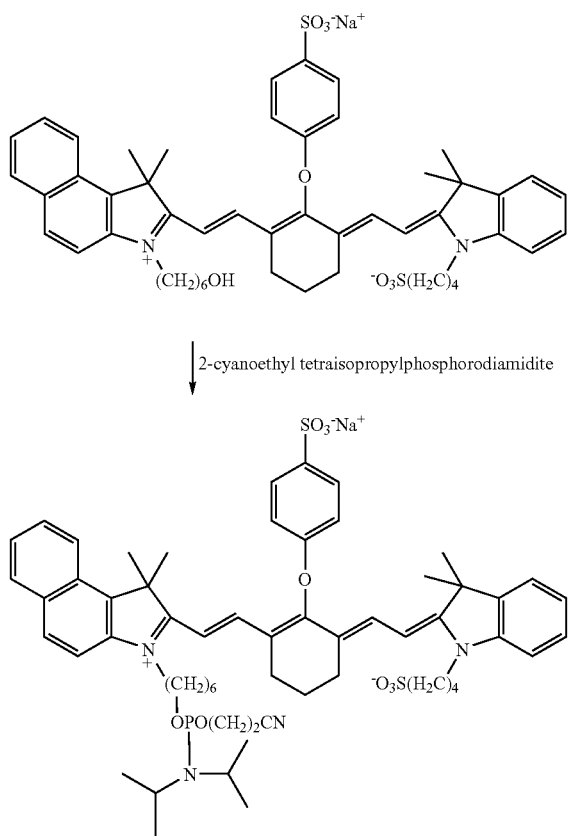

Synthesis of a sulfo-phenoxy dye: In 20 ml of dry methylene chloride was dissolved 1.4 g (1.59 mmol) of the above sulfo-phenoxy dye and the solution was cooled in an ice-acetone bath with stirring under nitrogen. After adding 0.6 g (1.01 ml; 3.18 mmol) of 2-cyanoethyl tetraisopropylphosphorodiamidite, and 0.045 g (1.3 ml; 0.64 mmol) of 1-H tetrazole solution (0.5M) at 0° C., the solution was stirred at room temperature for 2 to 2.5 h. Methylene chloride that contained 1% triethyl amine was added to the reaction mixture the reaction mixture was then subjected to washings with 5% sodium bicarbonate (50 ml×2) and water (50 ml×2). After drying over anhydrous sodium sulfate, the solution was filtered and the filtrate was concentrated to 5 ml. The concentrated solution was added at 0° C. to hexane (50 ml) under stirring and under nitrogen. The viscous residue obtained after the decantation of hexane was triturated with ether (50 ml) to give solid powder. It was dried under vacuum to give green powder of sulfo-phenoxy phosphoramidite (1.0 g; Yield 58%).

Example 4

Synthesizing an Intermediate Cyanine Dye

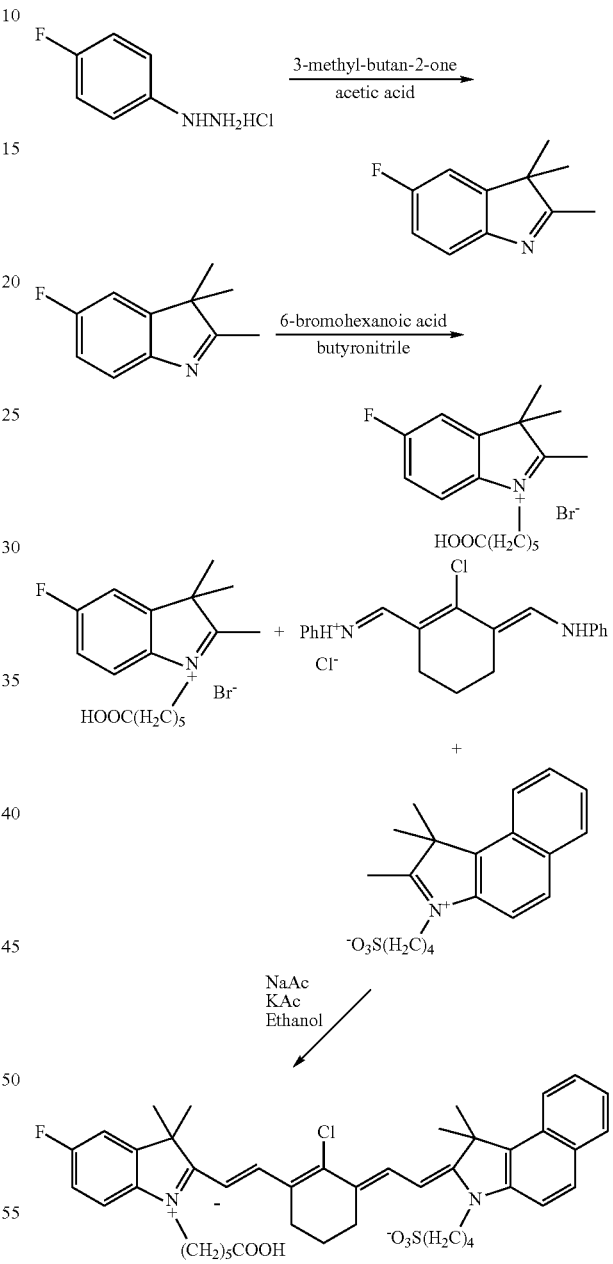

Step A: synthesis of 5-fluoro indole: A mixture containing 4-Fluorophenylhydrazine hydrochloride (5.0 g; 30.75 mmol; ALDRICH), 3-methyl-2-butanone (3.7 g; 43 mmol; ALDRICH) and acetic acid (30 ml) was stirred for 30 min. under nitrogen to obtain the clear solution. The mixture was then refluxed at 130° C. The appearance of UV-Vis Abs. Max at 255 nm and the disappearance of the peak at 282 nm confirmed the formation of the indole. At the end of 40 min. the reaction was stopped and the mixture was poured into crushed ice (100 g). The residue was extracted into ethyl acetate (100 ml×2), washed with water (100 ml×2) and ethyl acetate layer was dried over anhydrous sodium sulfate. After filtration, ethyl acetate was removed, and the residue was dried to give 4.15 g of the indole (Yield 76%).

Step B: synthesis of 5-fluoroindole carboxylate salt: A mixture containing 5-Fluoroindole (3.0 g; 16.9 mmol), 6-bromohexanoic acid (5.38 g; 27.6 mmol; ALDRICH), in butyronitrile 90 ml was refluxed under nitrogen at 140-145° C. The quaternization was complete after 35 to 40 h. The reaction mixture was cooled to room temperature and triturated with ether and finally dried under vacuum to give the solid (6.0 g; Yield 95%).

Step C: synthesis of benzindolesulfonate quaternary salt: This salt was prepared according to the procedure outlined for synthesizing indolesulfonate quaternary salt as described in Step A of Example 1.

Step D: synthesis of chloro dye: The product of step C was converted into a chloro dye using the procedure outlined in Step C of Example 1. In this case, 0.4 g (1 mmol) of 5-fluoroindole carboxylate salt and 0.35 g (1 mmol) of benzindole sulfonato were used to obtain 0.27 g (35% yield) of the chloro dye.

Example 5

Synthesizing a Cyanine Dye

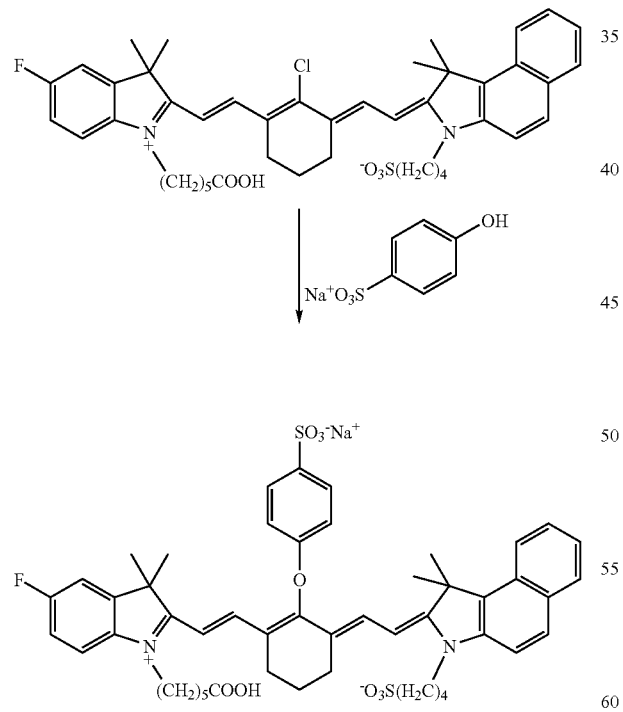

Synthesis of unsymmetrical sulfo-phenoxy dye: The chloro dye of Example 4 was converted into a sulfo-phenoxy dye using the procedure outlined in Example 2. Using 0.7 g (0.91 mmol) of the chloro dye, 0.4 g (48% yield) of the pure sulfo-phenoxy dye was obtained.

Example 6

Synthesizing an NHS Ester Cyanine Dye

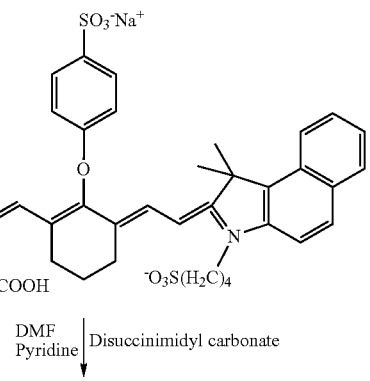

Synthesis of NHS ester dye: Carboxyalkyl dye (0.27 g; 0.3 mmol) that contained 5-fluoroindole and central sulfo-phenoxy group, was dissolved in a mixture of dry DMF (3.0 ml) and dry pyridine (0.3 ml). Disuccinimidyl carbonate (DSC, ALDRICH, 0.115 g; 0.44 mmol) was added and the mixture was stirred at 60° C. for 2 h. under nitrogen. After diluting the mixture with ether (15 ml), and decanting the supernatant, the product was redissolved in dry DMF (2 ml). Ether (15 ml) was added dropwise under stirring to give the solid precipitate. It was filtered, dried under vacuum to give 0.25 g of the reactive dye. (Yield 84%). The formation of the active ester was confirmed by HPLC.

Example 7

Synthesizing a Cyanine Dye

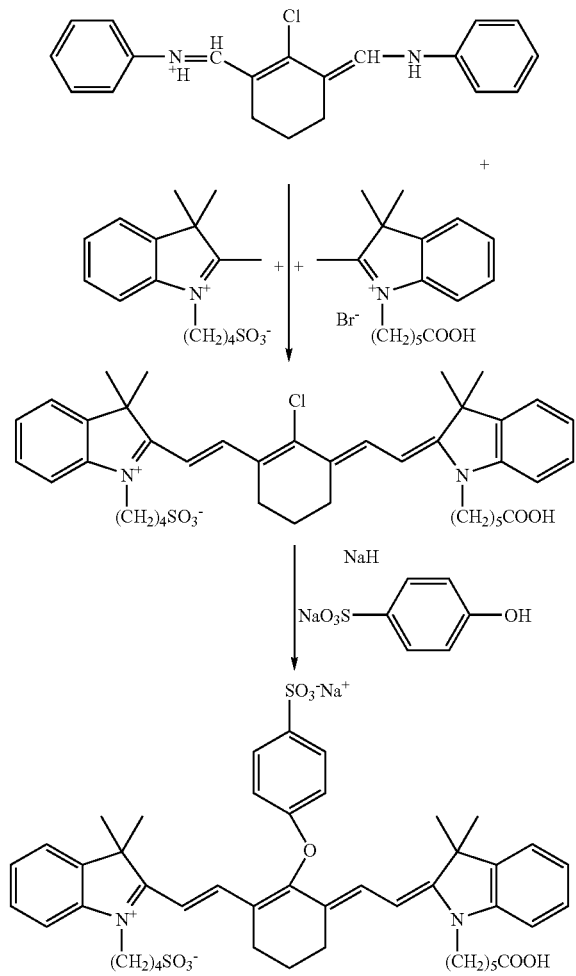

Step A: synthesis of 1-(4-sulfonatobutyl)-2,3,3-trimethylindolinine quatenary salt: A mixture of 1,2,3-trimethylindolenine (15.9 g, 100 mmol) and 1,4-butanesultone (27.2 g, 200 mmol) were heated to 140° C. in 250 ml of 1,2-dichlorobenzene for 16 h. The resulting gummy residue, separated by decanting the solvent was dissolved in minimum amount of methanol and precipitated with acetone. The pink precipitate was filtered and dried under vacuum. Yield: 85%

Step B: synthesis of 1-(6-carboxypentyl)-2,3,3-trimethylindolenine quaternary salt: A mixture of 1,2,3-trimethylindolenine (8 g, 50 mmol) and 6-bromohexanoic acid (19 g, 100 mmol) were heated to reflux in 250 ml of butyronitrile for 36 h. The resulting gummy residue, obtained after solvent removal by rotovap was dissolved in minimum amount of chloroform and precipitated with ether. The precipitate was triturated with ether to get a free flowing dry power. Yield: 70%

Step C: synthesis of chloro dye: A mixture of 5 mmol of each quaternary salts from Step A and Step B along with N-[(3-anilinoethylene)-2-chloro-1-cyclohexen-1-yl)-methylene]aniline monohydrochloride (1.30 g, 5 mmol), sodium acetate (1.1 g, 13 mmol) was refluxed in 30 ml of dry ethanol for 1 h. The reaction mixture was cooled down to remove ethanol by rotovap. The residue was chromatographed on a C 18 reversed phase silica gel column (methanol-water, 3:2) to obtain 30% of the desired chloro dye.

Step D: synthesis of sulfo-phenoxy dye: A solution of disodium salt of 4-hydroxybenzene sulfonic acid was prepared as follows: To a suspension of 60% sodium hydride (120 mg, 3 mmol of 100% NaH) in 10 ml of dry DMF, cooled to 0° C. under nitrogen was added a DMF solution (10 ml) of 4-hydroxy benzene sulfonic acid dihydrate, (2 mmol, ALDRICH). After 10 min. the reaction contents were warmed to room temperature for 20 min. Then, the contents were transferred to a flask containing 1 mmol of the chloro dye in 30 ml of DMF with vigorous stirring at room temperature. The reaction was monitored by UV-Vis absorption spectrum that showed a hypsochromic shift from 782 nm to 769 nm. After 30 min., the reaction was quenched with dry ice. DMF was evaporated on a rotovap. Precipitation with ether furnished the crude product as a dry powder that was further purified by reversed phase C18 silica by gel column using 40% aq. methanol. Yield 75%. The pure product was characterized by proton NMR.

Step E: synthesis of NHS ester of the sulfo-phenoxy dye: 2.6 mg of the sulfo-phenoxy dye (0.0031 mmol) was dissolved in 250 μL of dry DMF in a 1.5 ml micro centrifuge tube, to which was added 4.5 mg of N-hydroxysuccinimide (0.039 mmol, ALDRICH) and 10 mg of DCC (0.05 mmol, ALDRICH). The mixture was stirred at room temperature for 16 h and the progress of the reaction was monitored by HPLC. The excess reagents were removed by precipitation with ether and crude dye-NHSE was collected by centrifuging the precipitate, which was further purified by HPLC RPC 18 prep column (INERTSIL, ODS 3.5μ, 250×4.6 mm). It was eluted with a solvent gradient of buffer AB 90-10% to buffer 100% B (A=4% acetonitrile in 0.1M TEEAc and B=80% acetonitrile in 0.1M TEEAc). The fractions were pooled together and the solvent was removed by speed vac. to furnish 2 mg of pure ester. The presence of NHS ester was confirmed by HPLC.

Example 8

Synthesizing an NHS Ester Cyanine Dye

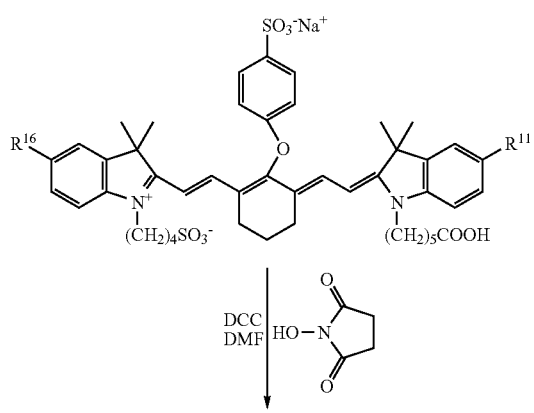

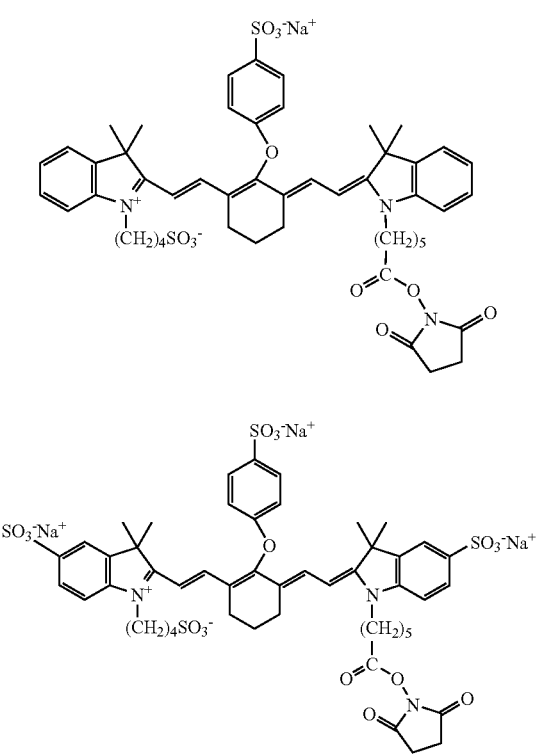

8a

8b

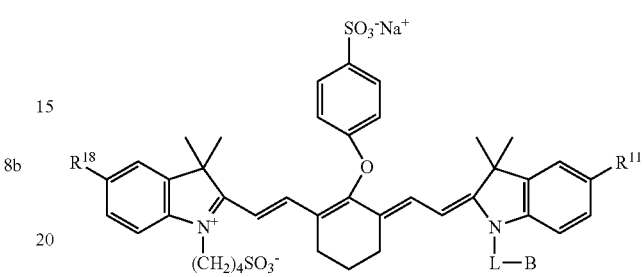

Synthesis of NHS ester dye 8a-8i: The carboxyalkyl dye of Example 7 (2.6 mg; 0.0031 mmol) was dissolved in dry DMF (250 µl). To this solution was added N-hydroxysuccinimide (ALDRICH; 4.5 mg; 0.039 mmol) and dicyclohexylcarbodiimide (DCC; ALDRICH; 10 mg; 0.05 mmol). The mixture was stirred at room temperature for 16 h. The reaction was monitored by HPLC and the NHS ester was purified by passing through RP column (INERTSIL, ODS 3.5µ, 250×4.6 mm) and eluting with a solvent gradient ranging from 10% b (a=4% acetonitrile in 0.1M triethylammonium acetate; b=80% acetonitrile in 0.1M in triethylammonium acetate) to 100% a. The solvent was removed under vacuum to give 2 mg of the pure NHS ester. The presence of reactive NHS ester group on dye 8a was confirmed by HPLC. Dyes 8b-8i (below) can be synthesized using analogous procedures.

| Dye | $R^{11}$ | $R^{16}$ |
|---|---|---|
| 8a | H | H |
| 8b | $SO_3^-$ | $SO_3^-$ |
| 8c | F | F |
| 8d | H | $SO_3^-$ |
| 8e | $SO_3^-$ | H |
| 8f | H | F |
| 8g | F | H |
| 8h | $SO_3^-$ | F |
| 8i | F | $SO_3^-$ |

Synthesis of various linkers: The procedure shown above can be carried out with a wide variety of linkers (L), for the attachment of the Dye to the biomolecule. For example, suitable linkers include a direct link, or a covalent linkage, wherein the covalent linkage is linear or branched, cyclic or heterocyclic, saturated or unsaturated, having 1-60 atoms selected from the group consisting of C, N, P, O, and S, wherein L can have additional hydrogen atoms to fill valences, wherein the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

For example, with reference to Table 1, column A is a list of the reactive functionalities, which functionalities can be on the dye or the biomolecule. Column B is a list of the complementary groups, either on the biomolecule or the dye (preferably, a carboxyl, hydroxyl, thiol, or amino functionality), which together with the reactive functionalities form a resulting bond of column C. The linking group comprises the resulting bond, and optionally additional atoms as stated above.

In certain aspects, the dye biomolecule conjugate from Examples 4 and 7 would have the following structures:

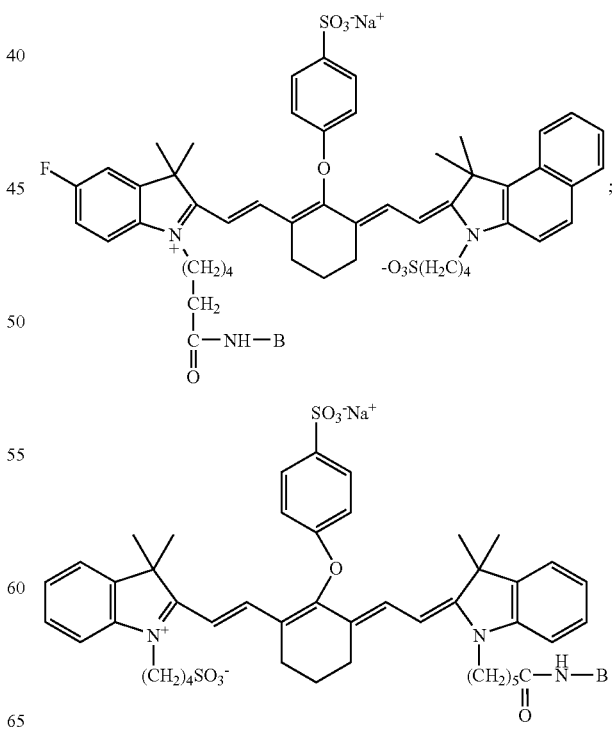

Example 9

Synthesizing a Dye-Labeled Acyclo-UTP

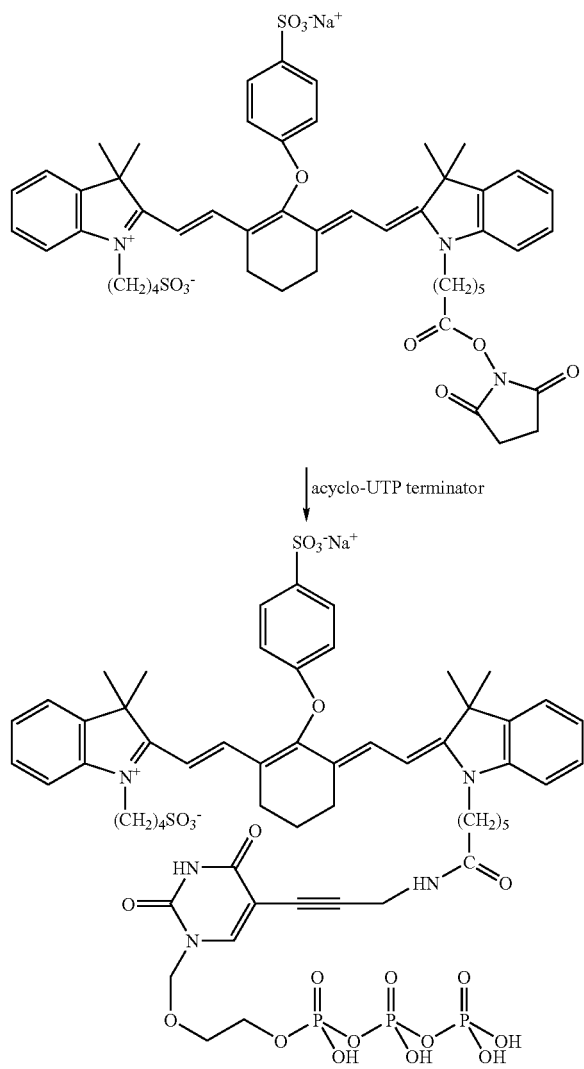

The dye of Example 8 was successfully conjugated to acyclo-terminators-ATP, GTP, CTP and UTP. These unlabeled terminators were obtained from NEN LIFE SCIENCE PRODUCTS, INC. Boston, Mass. The dye labeled terminators were purified in >95% purity by HPLC. Their concentrations were determined by UV-visible absorption spectra obtained in aqueous phosphate buffer. The labeled analogs were used in DNA sequencing and a high quality sequence ladder was obtained with the dye incorporated analogs. The dye labeled-Acyclo-UTP is illustrated above.

Example 10

Labeling DNA

The phosphoramidite of the sulfo-phenoxy dye of Example 2 was used to label DNA molecules prepared in a DNA synthesis machine. The dye was attached to the 5' end of the protected, support-bonded oligonucleotide via phosphoramidite deprotection chemistry. On syntheses at 200 mmol scale typical crude yields of phenoxy dye labeled oligonucleotides are 65 to 95 mmol. The sulfo-phenoxy dye-labeled oligonucleotides were obtained in 100 to 125 mmol.

Example 11

Stability of Sulfo-Phenoxy Dye in $NH_4OH$ & Dithiothreitol (DTT)

The sulfo-phenoxy dye of Example 2 and a counterpart phenoxy dye (200 mmol of ea.) of the same structure except with H in place of the sulfonate on the phenoxy dye were treated with 400 µl concentrated ammonium hydroxide and incubated at room temperature for 1 h. Another lot of 400 µl of concentrated ammonium hydroxide was added and stirred for additional 0.5 h. These are the conditions that are used in the deprotection of the dye-labeled primers. The reaction was followed at the interval of 15 min. by TLC. In case of phenoxy dye, the formation of the blue colored impurity was noticed at the end of 15 min. The intensity of this impurity increased as the time progressed. After 1.5 h, almost half of the dye was decomposed to give a blue dye. The blue spot was isolated and absorption and emission spectra were obtained. The blue colored impurity gave absorption maximum at 655 nm and emission at 747 nm. Under identical conditions, the sulfo-phenoxy dye did not form any blue colored spot that could be spotted by TLC or absorption. This shows clearly that the presence of the sulfonate group on the phenoxy improves the resistance of the dye to degradation by ammonia.

To study the resistance to attack by DTT, each of these two dyes (200 mmol each) was treated with 400 µl of DTT in acetonitrile and stirred at room temperature. After stirring overnight (16 h), TLC indicated the formation of new spots for the dye without the sulfonate on the phenoxy group. These degradation products were isolated and the UV/vis absorption spectra obtained. The three spots absorbed maximally at 786 nm, 738 nm and 392 nm, respectively. The absorption at 738 nm indicates the formation of new, degraded dye due to the decomposition of phenoxy dye that absorbs at 787 nm. The distinct impurity spot made its appearance only after 7 to 8 h. Under identical conditions overnight, sulfo-phenoxy dye of the Example 2 did not yield any spot that absorbs at 738 nm. Clearly, the presence of the sulfonate group on the phenoxy ring improves the resistance of the dye to attack by DTT.

The two dyes ("phenoxy" and "sulfo-phenoxy") have similar optical properties such as absorption maximum and extinction coefficient. These data show the unexpectedly improved stability obtained by replacing a hydrogen on the phenoxy ring with a sulfonate group. Since the stability problems are common to the cyanine dyes of this chemical family, similar improvement will also be obtained for the other dyes.

Dye-8a was used to label streptavidin. An amount of streptavidin was removed from the refrigerator and assayed by UV/vis to determine the amount. To this streptavidin was added 2.5 equivalents of Dye-8a. The labeling reaction (at pH 7.4) was allowed to proceed for 2 hours at 4° C. and then the reaction mixture was transferred into a 10K MWCO dialysis cassette. Dialysis was carried out for approximately 64 hours with a total of 3 buffer changes of 1 liter of 1×PBS each.

Analysis by UV/vis of the streptavidin after dialysis revealed that streptavidin was labeled with Dye-8a.

Example 12

A. Characterization of EGF-Dye 8b Conjugate

In Vitro Assays

Commercially available EGF was labeled on free amine groups using an NHS ester derivative of the Dye 8b of Example 8 in similar fashion to the streptavidin labeling of Dye-8b described directly above. The dye conjugate was purified by procedures well known to those of skill in the art. The specificity and activity of the EGF-Dye 8b were evaluated with confluent cultures of PC3M-LN4 and 22Rv1 cells using an in vitro microplate assay (In-cell Western; Chen, H., et al. 2005. *Anal. Biochem.* 338:136-142) scanned on Aerius™ (LI-COR® Biosciences, Lincoln, Nebr.). Biological activity of the conjugate was verified by its ability to stimulate EGF receptor kinase activity. FIG. 1 shows the outcome of specificity challenges performed in vitro. In panel A, binding of the EGF-Dye 8b probe to PC3M-LN4 and 22Rv1 cells is plotted. Panel B illustrates the low affinity of unconjugated Dye 8b and corresponds to the baseline level seen in Panel A. In panels C and D, binding of the labeled Dye 8b was effectively blocked by pre-treatment of cells with unlabeled EGF (C) or C225 (D) at 1.25 or 9.4 μg/mL, respectively.

B. In Vivo Animal Imaging

PC3M-LN4 or 22Rv1 cells ($10^6$) were implanted subcutaneously in the flank region of SCID mice (4 animals per cell type). Growth of tumors was monitored for 6 weeks by palpation, caliper measurement and optical imaging. For imaging, sterile-filtered EGF-Dye 8b probe (1-2 mmol per animal) was injected via the tail vein in isoflurane anesthetized mice. Images were then collected at the indicated time points. NIR fluorescence imaging of live animals was performed with a prototype LI-COR Biosciences small-animal imager. The LI-COR® instrument is a light-tight box equipped with a cooled CCD camera, area illumination via laser-diodes, and optical filters tuned for Dye 8b. Images were acquired and analyzed with Wasabi software from Hamamatsu Photonics (Hamamatsu City, Japan).

C. Image Analysis

Images analyzed in a series were normalized to the same LUT (Look Up Table) with a common minimum and maximum value for visual presentation. Regions of interest (ROIs) of equal area were used for both tumor and background regions. ROIs were quantified for total pixel and mean pixel values. The standard deviation of mean backgrounds was calculated using 3-5 ROIs. This calculation yields the number of standard deviations over background a suspect tumor would represent.

$$SNR = \frac{\text{(Mean Intensity tumor)} - \text{(Mean Intensity background)}}{\text{Standard deviation of mean background}}$$

D. Kinetics of Probe Clearance

Figure 2:
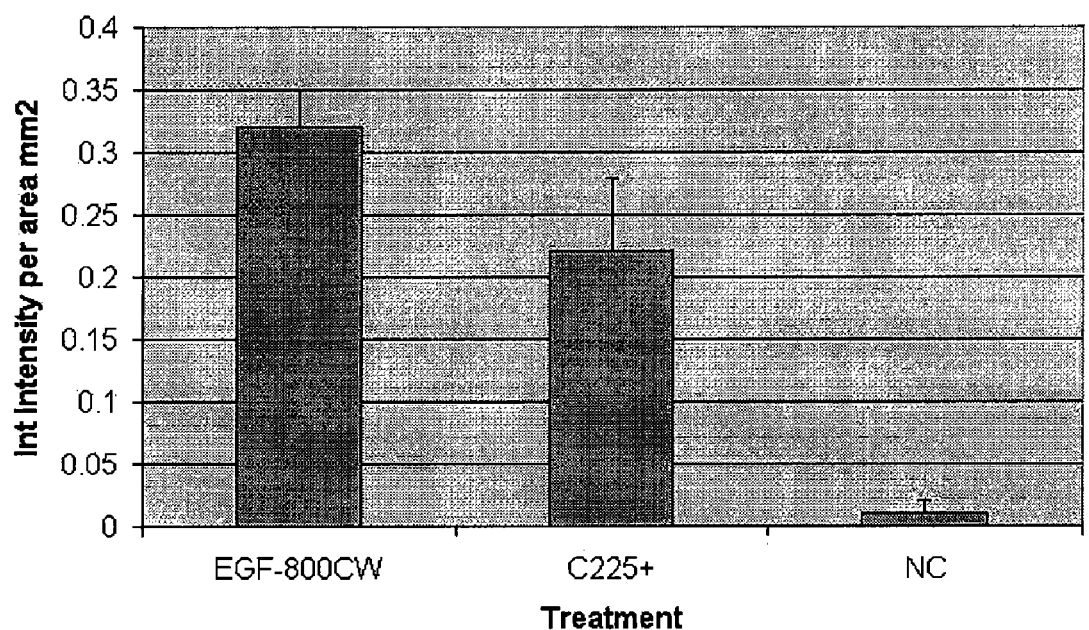
FIG. 2 shows a clearance profile of EGF-Dye 8b from a tumor-negative mouse over a 24-hour period.

Probe clearance from an animal with no tumor present was first evaluated. FIG. 2 illustrates clearance of EGF-Dye 8b over 24 hours. Two ROIs were analyzed. The large ROI covered the whole body core, while the small ROI focused on the abdominal region only.

Figure 3:
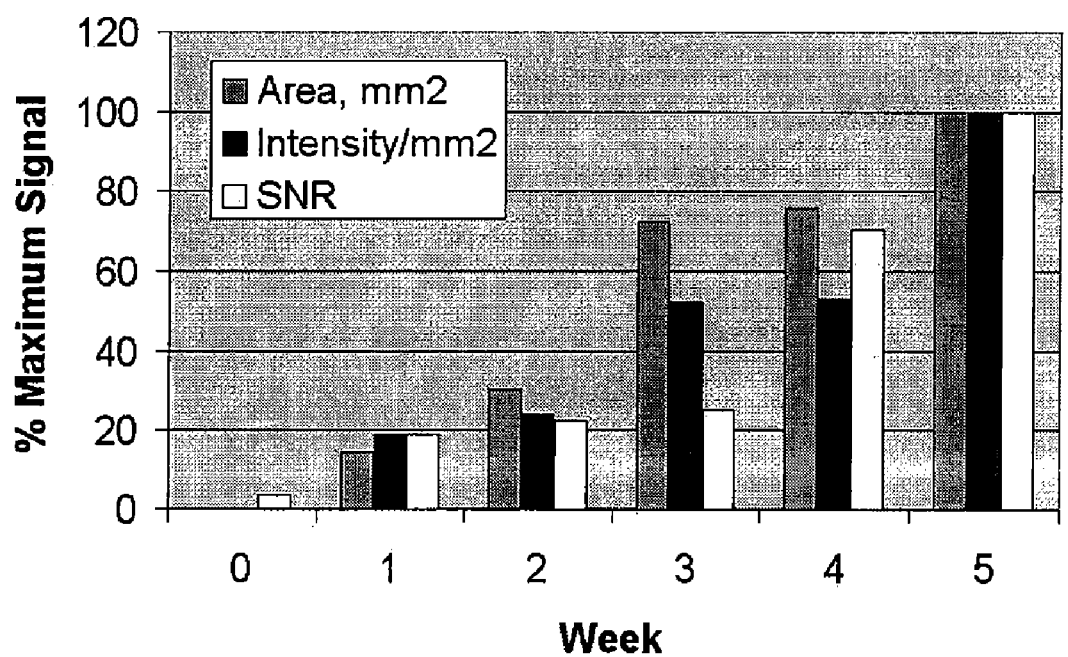
FIG. 3 shows a clearance profile of EGF-Dye 8b from a subcutaneous side tumor over a 96-hour time period.
Figure 4:
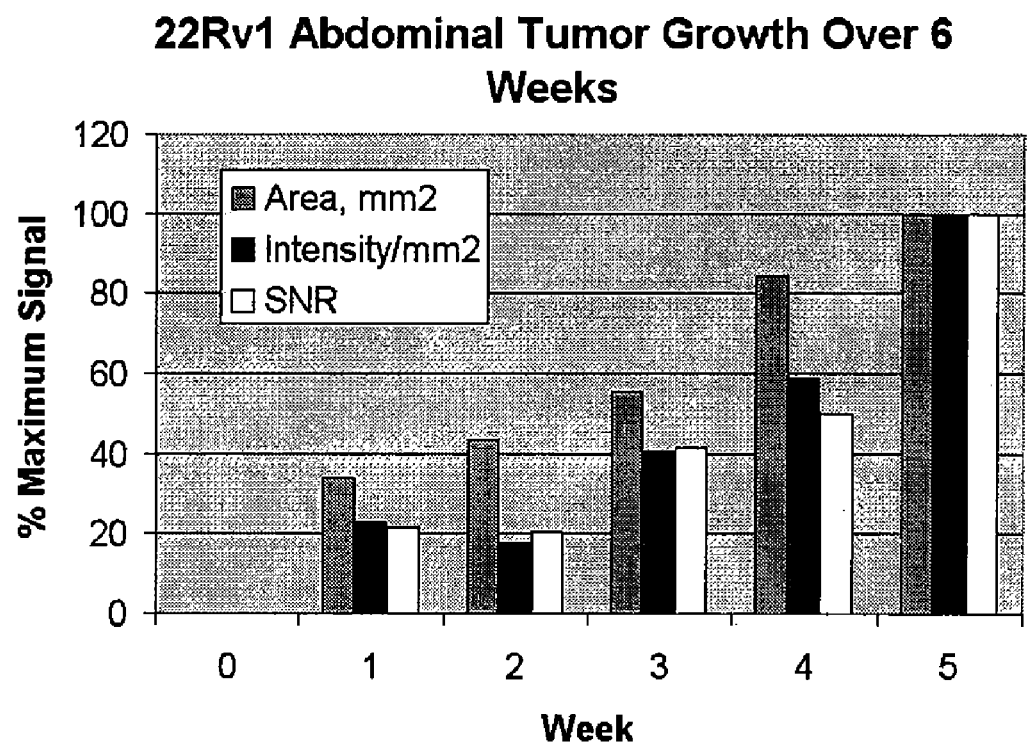
FIG. 4 shows the time course for PC3M-LN4 tumor growth over a 6-week period.
Figure 5:
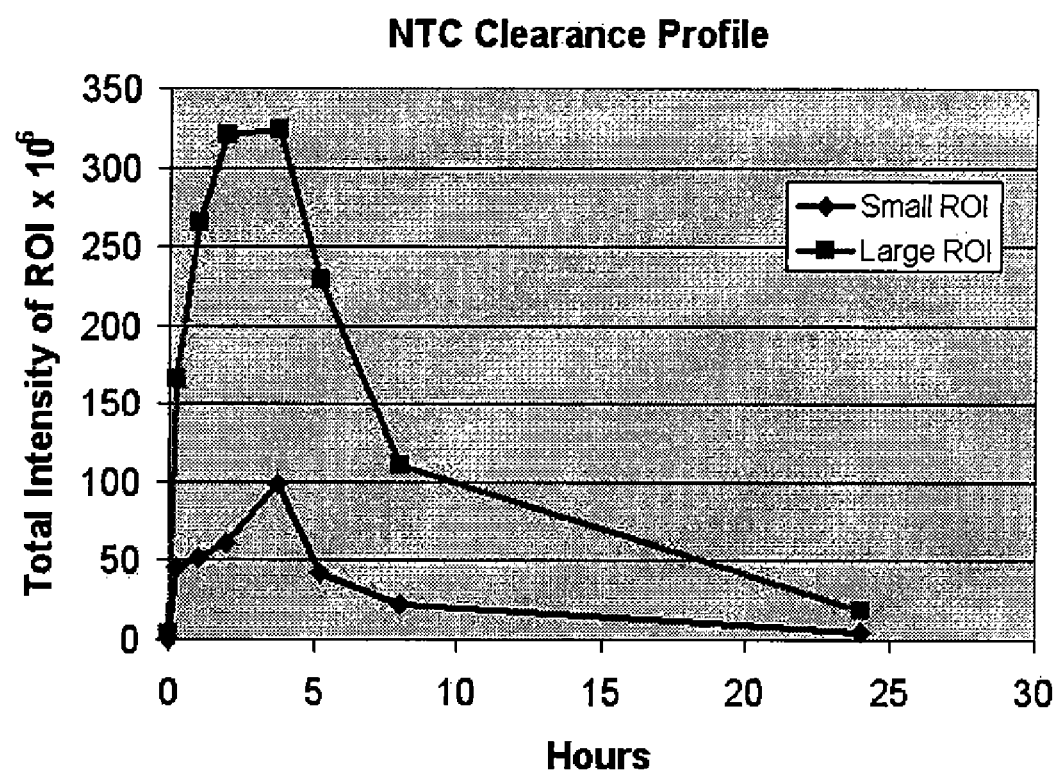
FIG. 5 shows the time course for 22Rv1 tumor growth over a 6-week period.
Figure 6:
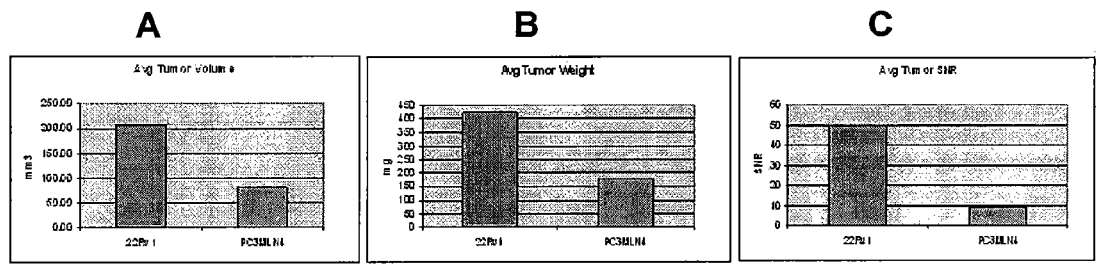
FIG. 6 (Panel A-C) shows averages for 22Rv1 and PC3M-LN4 prostate tumors after excision. Panel A is volume; Panel B is weight and Panel C is SNR calculated from images taken on week 6.

Results showed the peak signal for EGF-Dye 8b at 3.75 hours after injection, irrespective of ROI size. Accumulation in the bladder was clearly evident by 1 hour and 95% of total signal intensity had diminished by 24 hours. A tumor-positive animal was then evaluated for probe clearance using SNR as a measure. A series of images was taken to determine the optimal imaging time post-injection for a longitudinal study. After injection via the tail vein, the mouse was imaged at 0.3, 24, 48, 72, and 96 hours with the largest observed SNR achieved on day 4 (FIG. 3).

E. Early Detection of Tumors

Imaging began two weeks after SCID mice were implanted with tumor cells. Limit of detection was determined by evaluating an image that contained two small spots (<0.5 mm) in the area of interest. SNR were determined to be 3.20 and 2.43 for the two small spots on week 2. One week later, injection and imaging were repeated. The week 3 image in showed that the first spot is larger and confirmed as tumor signal by palpation, while the second spot was no longer visible and determined to be an artifact.

F. Tissue Section Analysis

A competitive challenge was conducted during week 5 with an animal receiving one of the following treatments: 1) EGF-Dye 8b (2 mmol); 2) Dye 8b only (3 nmol); 3) 2 mg/mL C225 (a monoclonal antibody for the EGF receptor, (Erbitux, ImClone) plus EGF-Dye 8b (2 nmol) 24 hours after C225 injection, and 4) 0.9% saline mock injection. After final imaging (day 4 post-injection), animals were sacrificed. Tumors were weighed, measured, and frozen sections prepared (0.8 μm thickness) for analysis on the Odyssey® Infrared Imaging System (LI-COR). Tissue section comparisons between EGF-Dye 8b and C225+EGF-Dye 8b showed a 54% decrease in signal when C225 was given 24 hours prior to EGF Dye 8b. When only Dye 8b was given, some signal was retained in the tumor, as also seen in vitro.

| Treatment | ID | Int 700 | Int 800 | Area (mm$^2$) | Int 800/ area (mm$^2$) | Avg |
|---|---|---|---|---|---|---|
| A) 0.9% Saline | C2P0 | 4.5 | 0.89 | 65.32 | 0.01 | 0.01 |
|  |  | 3.5 | 0.34 | 65.33 | 0.01 |  |
| B) Dye 8b | C2P2 | 1.45 | 18.7 | 30.06 | 0.62 | 0.56 |
|  |  | 1.24 | 13.18 | 26.22 | 0.50 |  |
| C) EGF-Dye 8b | C1P0 | 1.08 | 14.08 | 21.73 | 0.65 | 0.70 |
|  |  | 0.98 | 15.13 | 20.49 | 0.74 |  |
| D) C225 + EGF-Dye 8b | C1P2 | 2.27 | 15.43 | 39.49 | 0.39 | 0.38 |
|  |  | 1.99 | 13.71 | 37.86 | 0.36 |  |

Conclusions

As shown herein, the EGF-Dye 8b probe is specific and sensitive with respect to PC3M-LN4 and 22Rv1 prostate cancer cell lines, both in vitro and in vivo. This probe is also useful for other cancers, since the EGF receptor is elevated in many tumor models.

Example 13

A. Materials and Methods

Six-week-old male NOD/SCID mice were injected orthotopically with $10^5$ tumor cells. Two human prostate tumor cell lines were evaluated: PC3M-LN4, a highly tumorigenic and metastatic cell line, and 22Rv1 cells, previously uncharacterized in this model system. The biomarker, EGF-Dye 8b, was used for detection of tumors. On week 1, post-tumor cell implantation, 1 mmol of dye-conjugate was injected via the tail vein. A time course of dye clearance using signal to noise ratio (SNR) as a readout established the maximum specificity at 96 hours. Images were collected weekly for five weeks at 96 hours after dye injection. A competition challenge was included, in which C225 anti-EGF receptor blocking antibody was used to confirm specificity of the probe in the prostate tumors and lymph nodes.

Near-infrared fluorescence imaging of isoflurane-anesthetized live animals was performed with a prototype LI-COR® Biosciences small-animal imager (Lincoln, Nebr.). Images were acquired and analyzed with Wasabi software from Hamamatzu Photonics (Hamamatsu City, Japan).

At the termination of the study, tumors were imaged, excised, weighed, caliper measurements taken, and tissue sections prepared.

B. Results and Discussion

Figure 7:
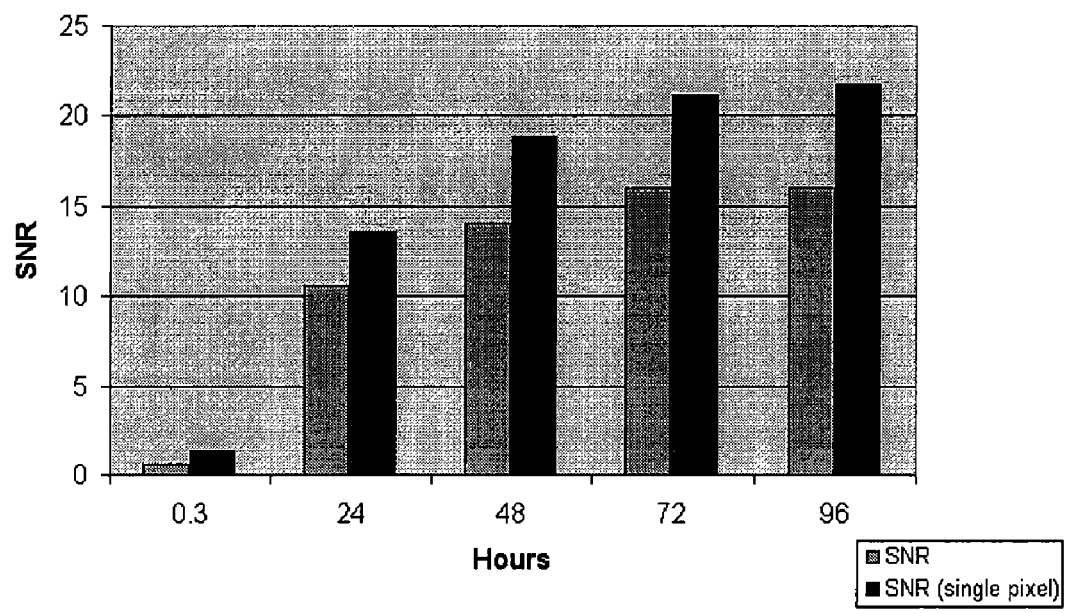
FIG. 7 illustrates comparisons of the lymph nodes from EGF-Dye 8b and C225+EGF-Dye 8b treatments.

When imaging internal tumor growth in a longitudinal study, a major concern is the ability to follow and correctly estimate tumor size. FIG. 7 (PC3M-LN4 tumor) and FIG. 8 (22Rv1 tumor) show the results for one animal gathered over the experiment's time period. Therefore, only pixels that met or exceeded the SNR standard in the region of interest were included in the estimation of tumor size over time. Area ($mm^2$), tumor signal intensity per $mm^2$, and peak SNR were determined. These parameters showed similar trends over time for both prostate tumor cell lines. Tumor growth was effectively monitored with EGF-Dye 8b in the orthotopic tumor model with tumor depths of up to 1 cm.

When tumor volume ($mm^2$), weight (mg), and SNR were compared, the 22Rv1 treatment group maintained a higher average in all analysis categories relative to PC3M-LN4 tumors (FIGS. 9, A, B and C respectively).

Further confirmation of the specificity of EGF-Dye 8b for the prostate tumors was achieved by recovering tumors and lymph nodes at the termination of the study.

Analysis showed that when C225, a monoclonal antibody that blocks the EGF receptor, was given 24 hours prior to the EGF-Dye 8b, approximately 39% blocking was achieved (FIG. 10). Deposition of the EGF-Dye 8b throughout the tumor was evident in both sections receiving labeled biomarker.

A primary objective of this study was to determine lymph node involvement with both cell lines and to evaluate EGF-Dye 8b as an indicator of metastasis. PC3M-LN4 is known to metastasize to the paraaortic lymph nodes, while 22Rv1 was uncharacterized. At the termination of the study, prostate tumors and lymph node regions were imaged in the open abdominal cavities. No enlargement or sign of metastases were noted for animals with 22Rv1 prostate tumors, even though those tumors were, on average, 3-fold larger by weight and volume compared to the PC3MLN4 prostate tumors. Lymph nodes for animals with PC3MLN4 prostate tumors appeared enlarged and opaque, visually exhibiting the characteristics of metastases. When imaging lymph nodes in an opened abdomen with a large prostate tumor, signal from the lymph nodes, though detected, is dampened by the high signal in the region. However, if the tumor is excised or covered, the signal in the lymph nodes is clearly evident.

Lymph nodes from the challenge animals were excised and scanned on Odyssey to confirm the presence of EGF-Dye 8b in paraaortic lymph nodes from the PC3M-LN4 animals. Although large prostate tumors developed in mice receiving 22Rv1 cells, these animals showed no signs of metastasis to the lymph nodes by week 6. The excised PC3M-LN4 nodes were analyzed in Odyssey and signal per area ($mm^2$) determined. Comparisons of the lymph nodes from EGF-Dye 8b and C225+EGF-Dye 8b treatments showed approximately 34% blockage in the lymph nodes compared to the 39% noted in the prostate tumors. These results suggest that the effect of C225 is extended to the site of metastasis, further confirming the specificity of the biomarker with this tumor model system.

|            | Channel | Intensity | Area, $mm^2$ | Signal/area, $mm^2$ | % Blocked |
|------------|---------|-----------|--------------|---------------------|-----------|
| NC         | 700     | 0.15      | 10.63        | 0.014               |           |
|            | 800     | 0.16      | 10.63        | 0.015               |           |
| EGF-Dye 8b | 700     | 0.14      | 6.26         | 0.022               |           |
|            | 800     | 7.20      | 6.26         | 1.150               |           |
| C225+      | 700     | 0.07      | 3.91         | 0.018               |           |
|            | 800     | 2.98      | 3.91         | 0.762               | 33.74     |

Lymph nodes from positive animals (PC3M-LN4 derived tumors) along with a negative control node (left). Green represents signal from 800 nm channel and red represents signal from the 700 nm channel (autofluorescence and background).

Conclusions

Unlike PC3M-LN4 tumors, 22Rv1 tumors exhibited no spontaneous metastasis to paraaortic lymph nodes, even with large prostate tumors present. Use of the EGF-Dye 8b biomarker and non-invasive optical fluorescent imaging allowed tumor size to be tracked in deep abdominal tumors, as well as in lymph nodes, confirming metastases and providing the researcher with immediate confirmation without the need for histology. In vivo signal antagonism by C225 antibody confirms the specificity of the EGF-Dye 8b biomarker.

Example 14

In vivo imaging of targeted molecular probes, or molecular imaging, is an emerging field for studying animal models of cancer, cardiovascular and neurodegenerative diseases. Optical imaging using fluorescently tagged targeting probes or tracers are particularly suited for molecular imaging, as fluorescent probes are safe, sensitive and can be specifically conjugated to small molecules, antibodies, peptides and proteins. Optical imaging has the potential to monitor growth and regression of tumors in a continuous and non-invasive fashion. Fluorophores with emissions in the visible region of the spectrum suffer from severe limitations to sensitivity due to autofluorescent background of tissues and blood. The most useful fluorescence agents have proven to be those with emissions in the range of 780-850 nm (see, Weissleder, Nature Biotechnology, Vol. 19, pp 316-317 (2001)). Because the absorbance spectra of bodily fluids and tissues exhibit local minima in the near-infrared (near-IR) region, imaging in the near-IR offers the advantages of relatively deep tissue penetration and low autofluorescence.

Advantages of having a bone marker or compound that can actively be taken into the bone during remodeling and resorption would provide landmarks for other imaging agents (an optical x-ray, if you will) or for research involving in osteoblastic metasteses. The targeting agent might also benefit those evaluating sites of mechanical injury which may expose binding sites for the agent. However, bone mineralization provides the most binding sites for the targeting agent. Certain stains are capable of binding during bone calcification, tetracyclines, green fluorescein derivatives such as calcein or DCAF among others. We have utilized a known fluorochrome (calcein, excitation 488 and emission 520 nm) and tagged it with Dye 8b of Example 8 to achieve two objectives: 1) to incorporate the compound into actively growing bone and move the detection of the compound into the NIR region to take advantage of the higher sensitivity of detection and 2) to produce a duel labeled compound for more versatility.

B. Synthesis

1) The starting material, calcein, was purchased as a single pure isomer, and one of its carboxylate groups was activated by TSU in the presence of DIPEA in DMSO.

2) The NHS ester activated carboxylate group was then conjugate to Boc-protected ethylene diamine (EDA) to generate a potential primary amine carrying calcein derivative.

3) The Boc protecting group was removed with TFA to liberate the primary amine on the calcein-EDA. And this precursor, calcein-EDA, was purified by HPLC before final Dye 8b conjugation.

4) The final bone marker—calcein-Dye 8b—was obtained by conjugating the above calcein-EDA with Dye-8b NHS ester with one-to-one mole ratio. This product is further purified by HPLC to removed Dye-8b free acid and calcein-EDA. After HPLC purification, the product was dried on a speed-vac at room temperature, and then was stored in a −20° C. freezer until needed.

The synthesis was tracked by HPLC and MS all the way along. The above procedures can be summarized in the following synthetic scheme (the product below is a mixture of isomers).

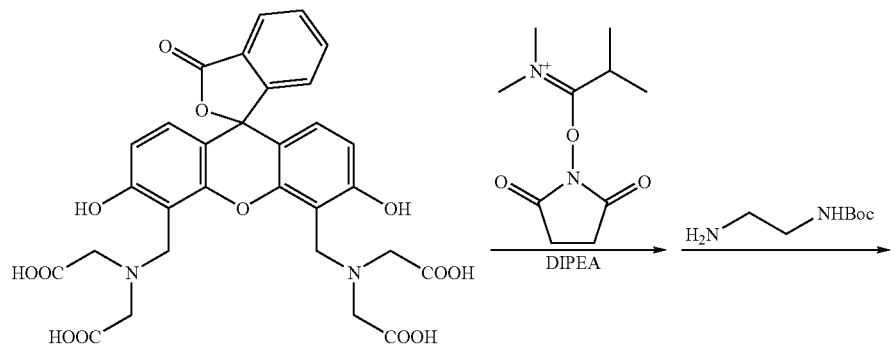

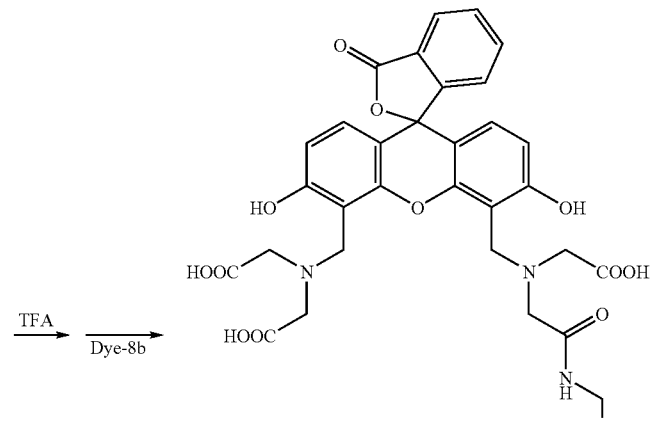

-continued

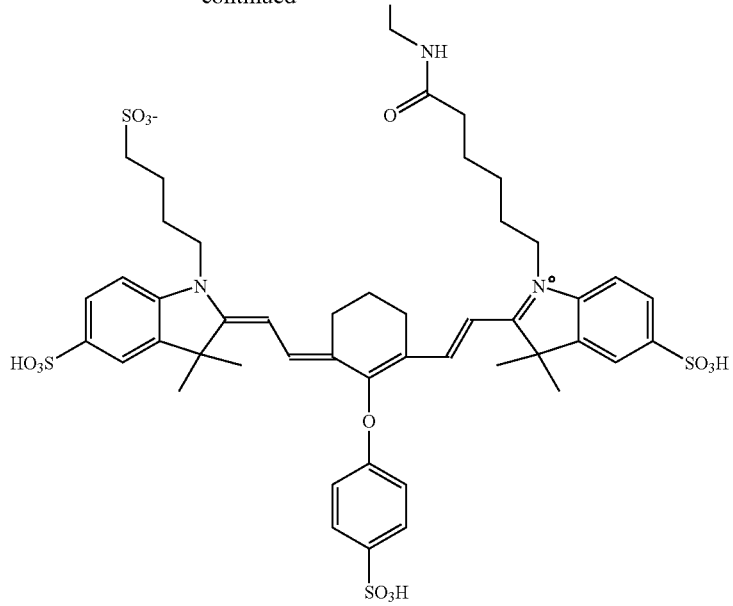

SCOPE

It is intended that the foregoing detailed description, including its examples, be regarded as illustrative rather than limiting, and that it be understood that the following claims, including all equivalents, are intended to define the scope of this invention.

What is claimed is:

1. A compound of the formula:

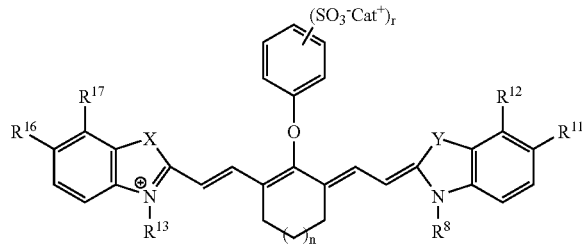

wherein $Cat^+$ is a cation;
r is an integer equal to 1, 2 or 3;
X and Y are each independently O, S, Se, or $(CH_3)_2C$; and
$R^8$ and $R^{13}$ are each independently alkyl, L—$R^{25}$ or L—B; wherein at least one of $R^8$ and $R^{13}$ is L—B;
$R^{25}$ is a member selected from the group consisting of optionally substituted alkyl, hydroxyl, thioacetyl and sulfanato;
L is a linker;
B is a ligand;
n is 0, 1, 2 or 3;
$R^{11}$ and $R^{12}$ are each independently F, H, sulfonato, or together with the atoms to which they are bonded form an aromatic ring; and
$R^{16}$ and $R^{17}$ are each independently H, sulfonato, or together with the atoms to which they are bonded form an aromatic ring.

2. The compound of claim 1, wherein
r is 1;
$R^{11}$ and $R^{12}$ are each independently F, H, or sulfonato;
$R^{16}$ and $R^{17}$ are each independently F, H, or sulfonato; and
n is 1.

3. The compound of claim 1, wherein $Cat^+$ is $H^+$ or a metal ion.

4. The compound of claim 1, wherein at least one of X and Y is $(CH_3)_2C$.

5. The compound of claim 1, wherein L is a member selected from the group consisting of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

6. The compound of claim 1, wherein L is a member selected from the group consisting of a PEG, a block copolymer of PEG-polyurethane and a PEG-polypropylene.

7. The compound of claim 1, wherein L is a member selected from the group consisting of a polysaccharide, a polypeptide, an oligosaccharide, a polymer, a co-polymer and an oligonucleotide.

8. The compound of claim 5, wherein L is of the formula:

—$X^1$—$Y^1$—$X^2$— wherein:
$X^1$ is a member selected from the group consisting of a bivalent radical, a direct link, oxygen, an optionally substituted nitrogen and sulfur;
$Y^1$ is a member selected from the group consisting of a direct link and $C_1$-$C_{10}$ alkylene optionally interrupted by a heteroatom; and X² is a member selected from the group consisting of a bivalent radical, a direct link, oxygen, an optionally substituted nitrogen and sulfur.

9. The compound of claim 5, wherein the bivalent radical of X¹ and X² are each independently selected from the group consisting of a direct link, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

10. The compound of claim 8, wherein L is —(CH₂)ᵣ—, wherein r is an integer from 1 to 50.

11. The compound of claim 1, wherein both R⁸ and R¹³ are L—B.

12. The compound of claim 10, wherein r is an integer from 1 to 5.

13. The compound of claim 1, wherein the compound has the structure of:

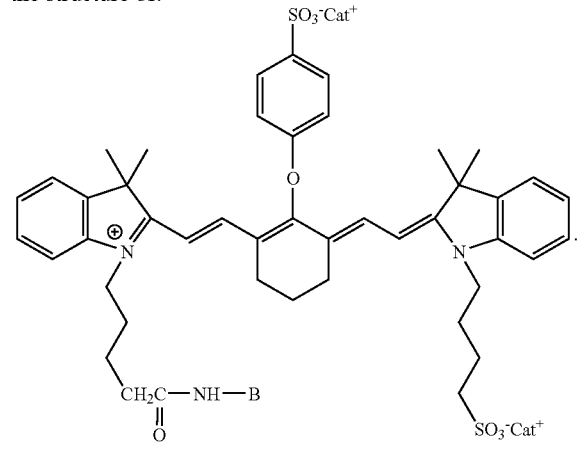

14. The compound of claim 1, wherein the compound has the structure of:

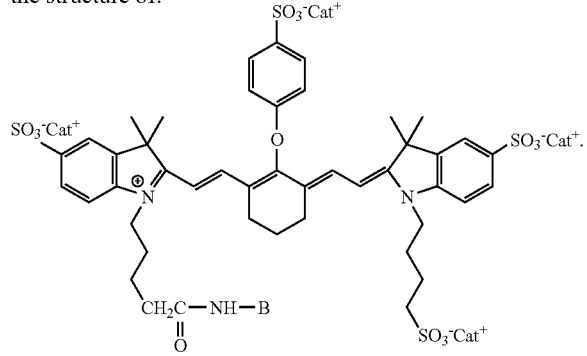

15. The compound of claim 1, wherein the compound has the structure of:

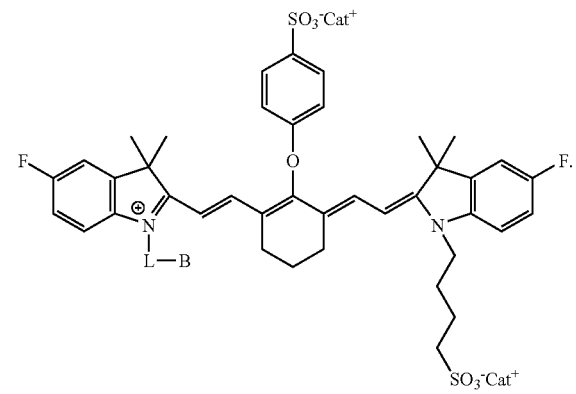

16. The compound of claim 1, wherein the compound has the structure of:

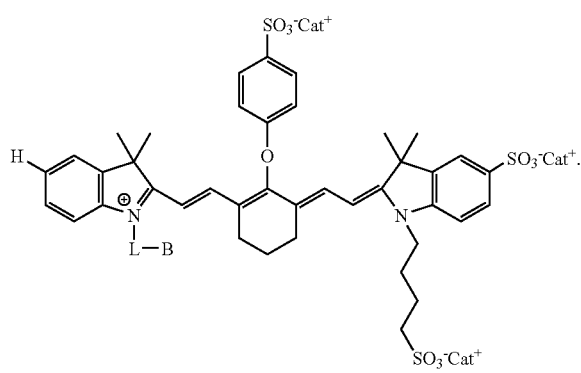

17. The compound of claim 1, wherein the compound has the structure of:

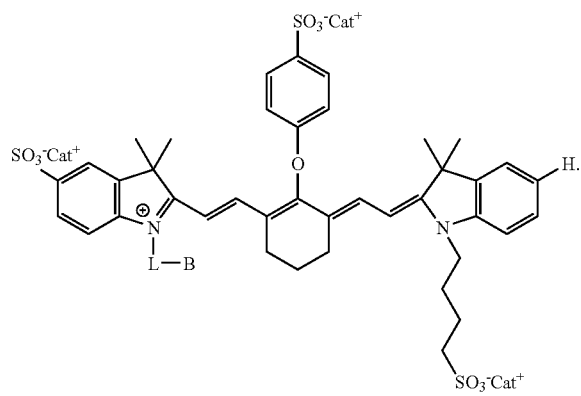

18. The compound of claim 1, wherein the compound has the structure of:

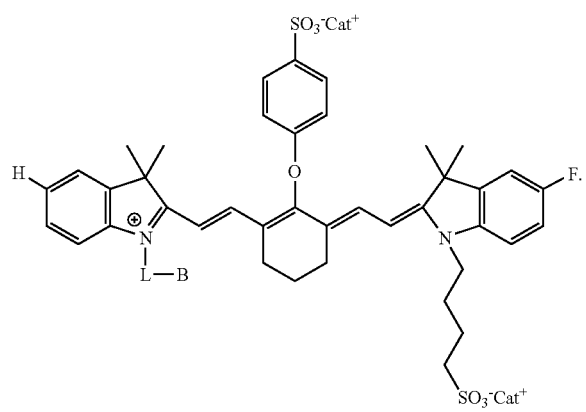

19. The compound of claim 1, wherein the compound has the structure of:

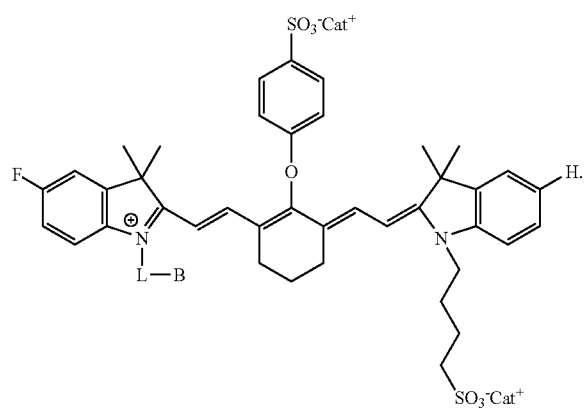

20. The compound of claim 1, wherein the compound has the structure of:

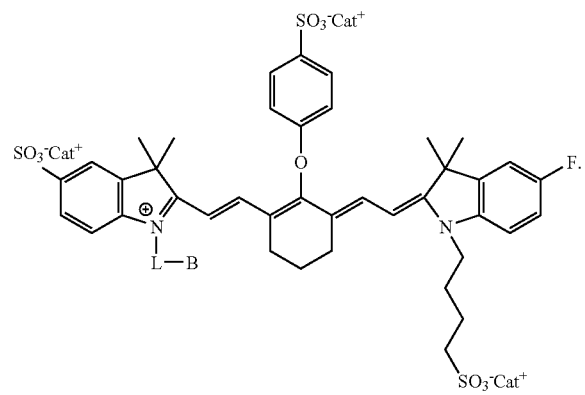

21. The compound of claim 1, wherein the compound has the structure of:

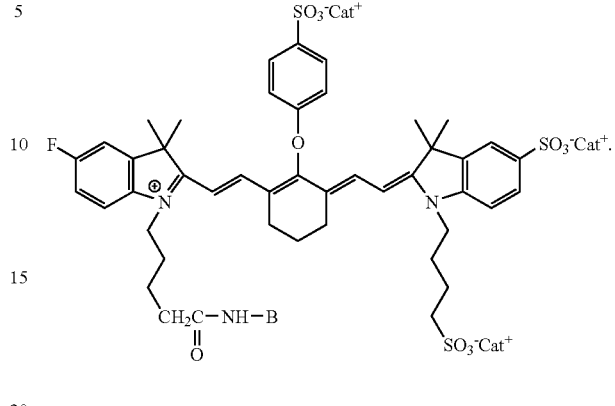

22. The compound of claim 1, wherein B is a ligand that has affinity for a receptor selected from the group consisting of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocordicosteroid receptor, Retinoid-X receptor, RHAMM, high affinity folate receptors, Met receptor, estrogen receptor and Ki67.

23. The compound of claim 1, wherein B is selected from the group consisting of somatostatin, endostatin, a carbohydrate, a monosaccharide, a disaccharide, a trisaccharide, an oligosaccharide, aptamer, liposome and PEG.

24. The compound of claim 1, wherein B is 2-deoxy-D-glucose, 2-deoxy-D-glucosamine, a glucose derivative, glyceraldehydes, erythrose, threose, ribose, arabinose, xylose, lyxose, allose, altrose, glucose, mannose, gulose, idose, galactose, talose, erythrulose, ribulose, xylulose, psicose, fructose, sorbose, and tagatose.

25. The compound of claim 1, wherein B is selected from the group consisting of angiopoietins, angiostatin, angiotensin II, $\alpha_2$-antiplasmin, annexin V, $\beta$-cyclodextrin tetradecasulfate, endoglin, endosialin, endostatin, epidermal growth factor, fibrin, fibrinopeptide $\beta$, fibroblast growth factor, FGF-3, basic fibronectin, fumagillin heparin, hepatocyte growth factor, hyaluronan, insulin-like growth factor, interferon-$\alpha$, $\beta$ inhibitors, IL inhibitor, laminin, leukemia inhibitory factor, linomide, metalloproteinases, metalloproteinase inhibitors, antibodies, antibody fragments, monoclonal antibody fragments, cyclic $RGD_D$ FV, placental growth factor, placental proliferin-related protein, plasminogen, plasminogen activator, plasminogen activator inhibitor-1, platelet activating factor antagonists, platelet-derived growth factor, platelet-derived growth factor receptors, platelet-derived endothelial cell growth factor, pleiotropin, proliferin, proliferin-related protein, selectins SPARC, snake venoms, substance P, suramin, tissue inhibitor of metalloproteinases, thalidomide, thrombin, thrombin-receptor-activating tetradecapeptide, transforming growth factor-$\alpha$, $\beta$, transforming growth factor receptor, tumor growth factor-$\alpha$, tumor necrosis factor and vitronectin.

26. The compound of claim 25, wherein B is epidermal growth factor.

27. The compound of claim 1, wherein B is a compound with selected from the group consisting of a tetracycline bone binding agent and a green fluorescein bone binding agent.

28. The compound of claim 27, wherein B is calcein.

29. The compound of claim 1, wherein the covalent linkage between L and B is selected from the group consisting of a direct bond, an amide bond, an ester bond, an ether bond, an oxime bond, a phosphate ester bond, a sulfonamide bond, a thioether bond, a thiourea bond, and an urea bond.

30. A method for generating an image of a subject, said method comprising:

administering a compound of claim 1 to said subject; and generating an image of said subject, wherein said compound has been distributed.

31. The method of claim 30, wherein said compound has been distributed to a tumor.

32. The method of claim 30, wherein said compound has been distributed to bone.

33. The method of claim 30, wherein said compound has been distributed to a tissue or an organ.

34. The method of claim 30, wherein said subject is a human.

35. The compound of claim 25, wherein the metalloproteinase is matrix metalloproteinase-2.

36. The compound of claim 25, wherein the selectin is an E-selectin.

37. The compound of claim 25, wherein the antibodies are monoclonal antibodies.

38. The compound of claim 25, wherein the antibody fragments are monoclonal antibody fragments.

* * * * *

UNITED STATES PATENT AND TRADEMARK OFFICE
CERTIFICATE OF CORRECTION

| | | |
|---|---|---|
| PATENT NO. | : 7,597,878 B2 | |
| APPLICATION NO. | : 11/419457 | |
| DATED | : October 6, 2009 | |
| INVENTOR(S) | : Joy Kovar et al. | |

It is certified that error appears in the above-identified patent and that said Letters Patent is hereby corrected as shown below:

Claim 25, Column 60, line 48 and 49:

"antibodies, antibody fragments, monoclonal antibody fragments, cyclic $RGD_DFV$, placental growth factor, placental"

Should read

-- antibodies, antibody fragments, cyclic $RGD_DFV$, placental growth factor, placental --

Signed and Sealed this
First Day of March, 2011

David J. Kappos
*Director of the United States Patent and Trademark Office*